US012620466B1

(12) United States Patent
Hunt et al.

(10) Patent No.: US 12,620,466 B1
(45) Date of Patent: *May 5, 2026

(54) COMPUTER-BASED TOOLS AND TECHNIQUES FOR ANALYZING HEALTH CARE DATA IN CONNECTION WITH MEDICAL PROCEDURES

(71) Applicant: MEDCOM SOLUTIONS, INC., Pittsburgh, PA (US)

(72) Inventors: William A. Hunt, Pittsburgh, PA (US); Ziwei Yi, Pittsburgh, PA (US)

(73) Assignee: MEDCOM SOLUTIONS, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,160

(22) Filed: Feb. 28, 2024

Related U.S. Application Data

(63) Continuation of application No. 18/151,380, filed on Jan. 6, 2023, now Pat. No. 11,923,055.

(60) Provisional application No. 63/297,181, filed on Jan. 6, 2022.

(51) Int. Cl.
*G16H 15/00* (2018.01)
*G16H 10/60* (2018.01)

(52) U.S. Cl.
CPC .................................. *G16H 15/00* (2018.01)

(58) Field of Classification Search
CPC ....................................................... G16H 15/00
See application file for complete search history.

(56) References Cited

U.S. PATENT DOCUMENTS

2006/0085221 A1* 4/2006 Lipsky ................... G06Q 10/10
                                                                705/2
2019/0355455 A1* 11/2019 Mander .................. G16H 15/00

* cited by examiner

*Primary Examiner* — Maroun P Kanaan
(74) *Attorney, Agent, or Firm* — Leech Tishman Fuscaldo & Lampl, LLC

(57) ABSTRACT

Tools and techniques are provided for analyzing health care procedure related transactions of a health care entity. The method can include creating a linked data items file, by a transaction analysis computer system, derived from a combination of a charge description master (CDM) file containing CDM data items, an order entry system (OES) file containing OES data items, and a CDM-to-OES cross-reference data file. The linked data items file can be analyzed by reading linked line items, analyzing its CDM data portion, analyzing its OES data portion, and/or comparing the linked CDM data portion to the linked OES data portion for determining similarities or differences between the CDM and OES data portions.

17 Claims, 25 Drawing Sheets

802

OES items not mapped to CDM item with email notification date and person notified

804

CDM items not mapped to OES item with email notification date and person notified

STOP

CDM TO ORDER ENTRY MAPPING SUMMARY

Add Linked Dataset

Name

CANCEL

SAVE

FIG. 16

Linked Data for 20060003

REVENUE USAGE   OSCSUPPLY

| VOL.YTDTotal | REV.YTDTotal | IP_OP | FC | Facility |
|---|---|---|---|---|
| 100 | 18072 | Inpatient | SELF PAY | Hospital8 |
| 0 | 0 | Inpatient | SELF PAY AFTER INS | Hospital2 |

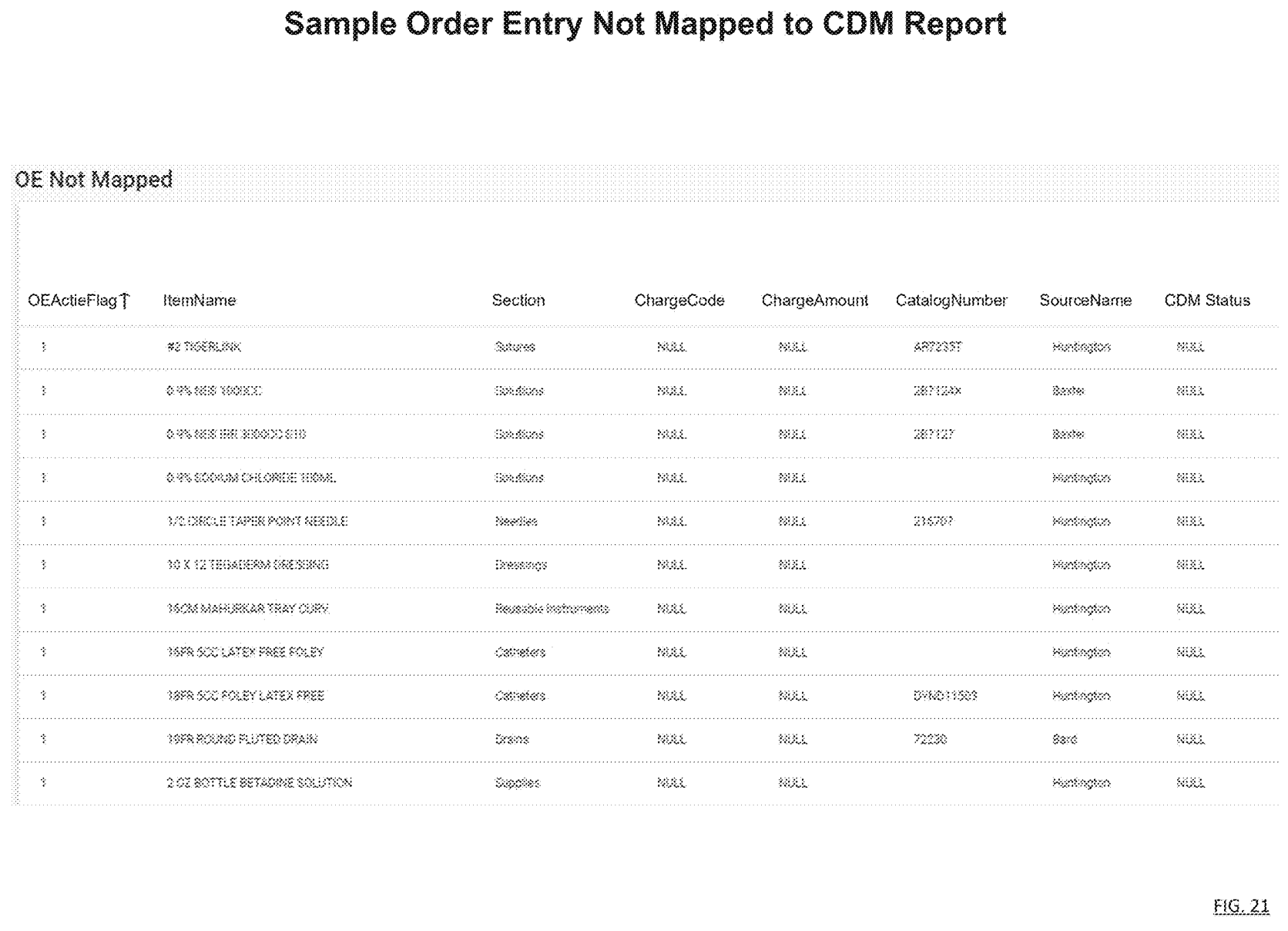

Sample Order Entry Not Mapped to CDM Report

OE Not Mapped

| OEActieFlag | ItemName | Section | ChargeCode | ChargeAmount | CatalogNumber | SourceName | CDM Status |
|---|---|---|---|---|---|---|---|
| - | #2 TIGERLINK | Sutures | NULL | NULL | ARF235T | Huntington | NULL |
| - | 0-PK AEEB VICRYL | Sutures | NULL | NULL | 2857-12AX | Boston | NULL |
| - | 0-PK AEEB BRE BRO072-6110 | Sutures | NULL | NULL | 2857727 | Boston | NULL |
| - | 0-PK ECAVAM CHLORBIE NEDAL | Sutures | NULL | NULL | | Huntington | NULL |
| - | 1.0.DBKCH TAPER POINT NEEDLE | Needles | NULL | NULL | 235707 | Huntington | NULL |
| - | 10 X 12 TELFA HERWA DRESSING | Dressings | NULL | NULL | | Huntington | NULL |
| - | 16CM AAAHUKKAR TRAY COPY | Reusable instruments | NULL | NULL | | Huntington | NULL |
| - | 18FR SCO LATEX FREE FOLEY | Catheters | NULL | NULL | | Huntington | NULL |
| - | 18FR SCO FOLEY LATEX FREE | Catheters | NULL | NULL | DFMO71920 | Huntington | NULL |
| - | 18FR ROUND FLUTED DRAIN | Drains | NULL | NULL | 7228 | Bard | NULL |
| - | 2 OZ BOTTLE BETADINE SOLUTION | Supplies | NULL | NULL | | Huntington | NULL |

FIG. 21

Figure 22:
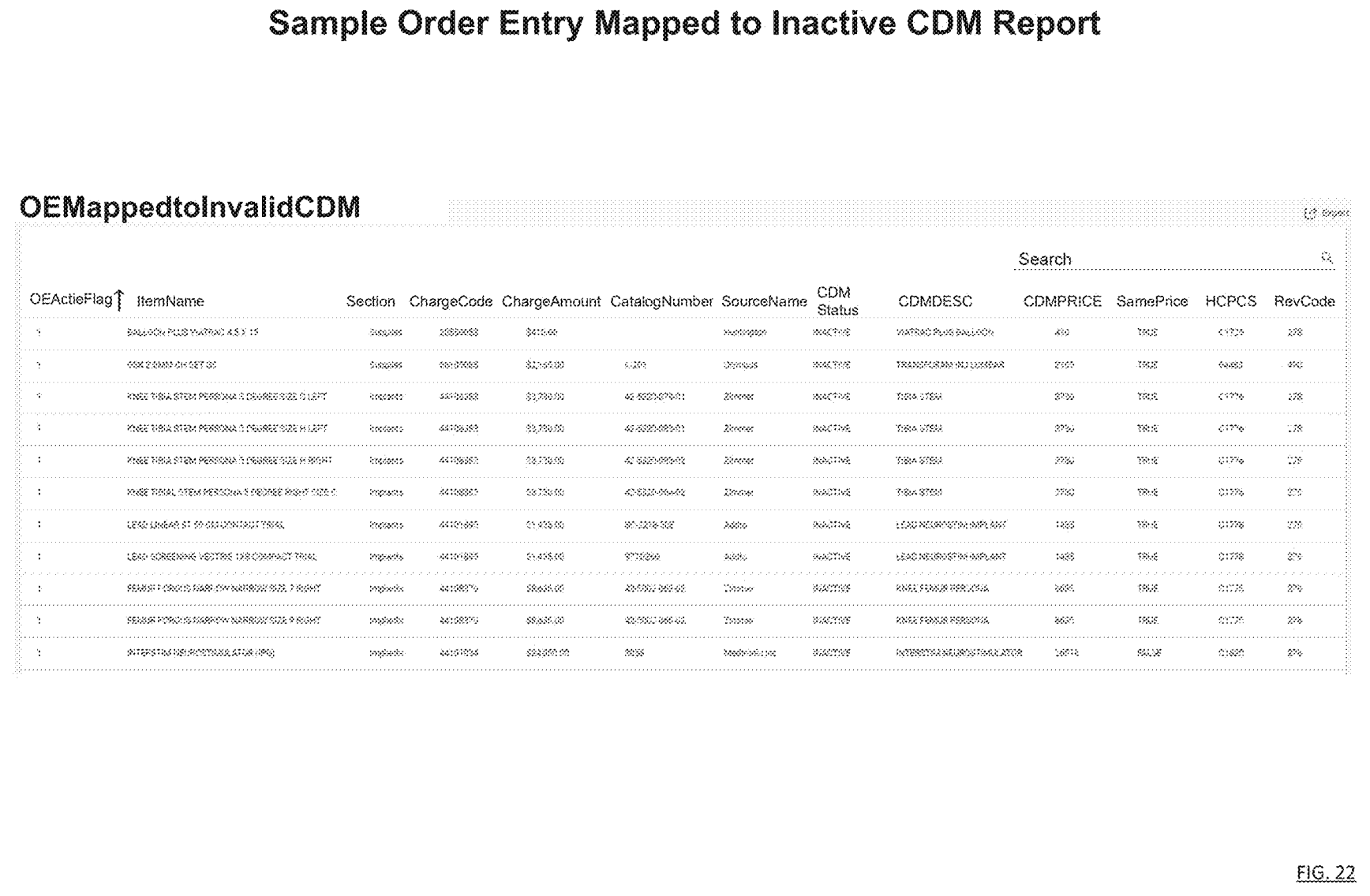

Sample Order Entry Mapped to Inactive CDM Report

OEMappedtoInvalidCDM

Search

| OEActiveFlag | ItemName | Section | ChargeCode | ChargeAmount | CatalogNumber | SourceName | CDM Status | CDMDESC | CDMPRICE | SamePrice | HCPCS | RevCode |
|---|---|---|---|---|---|---|---|---|---|---|---|---|

COMPUTER-BASED TOOLS AND TECHNIQUES FOR ANALYZING HEALTH CARE DATA IN CONNECTION WITH MEDICAL PROCEDURES

CROSS-REFERENCE TO RELATED APPLICATION/PRIORITY CLAIM

This application claims the benefit of U.S. application Ser. No. 18/151,380, filed on Jan. 6, 2023, which claims priority to U.S. provisional patent application Ser. No. 63/297,181, filed on Jan. 6, 2022, the entirety of which is hereby incorporated by reference into the present application.

FIELD OF THE INVENTION

In various embodiments, the present invention generally relates to computer-based tools, devices, and processes for analyzing records and other information associated with administering health care treatments to patients at a health care facility.

BACKGROUND

In the health care industry, charging for clinical procedures, visits and services are highly governed by Medicare, Medicaid and other commercial payors. Clinical activity including various medical procedures must be appropriately charged to the responsible party using diagnostic codes and procedure codes. These body of code sets are the means to which an insurer will acknowledge the services provided and the basis for payment of such patient care. If such charging is performed incorrectly or inefficiently, this can negatively impact the ability of a health care facility to provide medically effective and cost effective health care.

What are needed, therefore, are improved tools and techniques for analyzing data associated with performing medical procedures at health care facilities and their associated charges. This would lead to providing more efficient and effective medical procedures for patients who need health care.

BRIEF DESCRIPTION OF THE FIGURES

FIG. 11 through 14 include screen displays illustrating examples of a "Configurations" section of a navigator application configured for use in connection with a transaction analysis system software.

Figure 16:
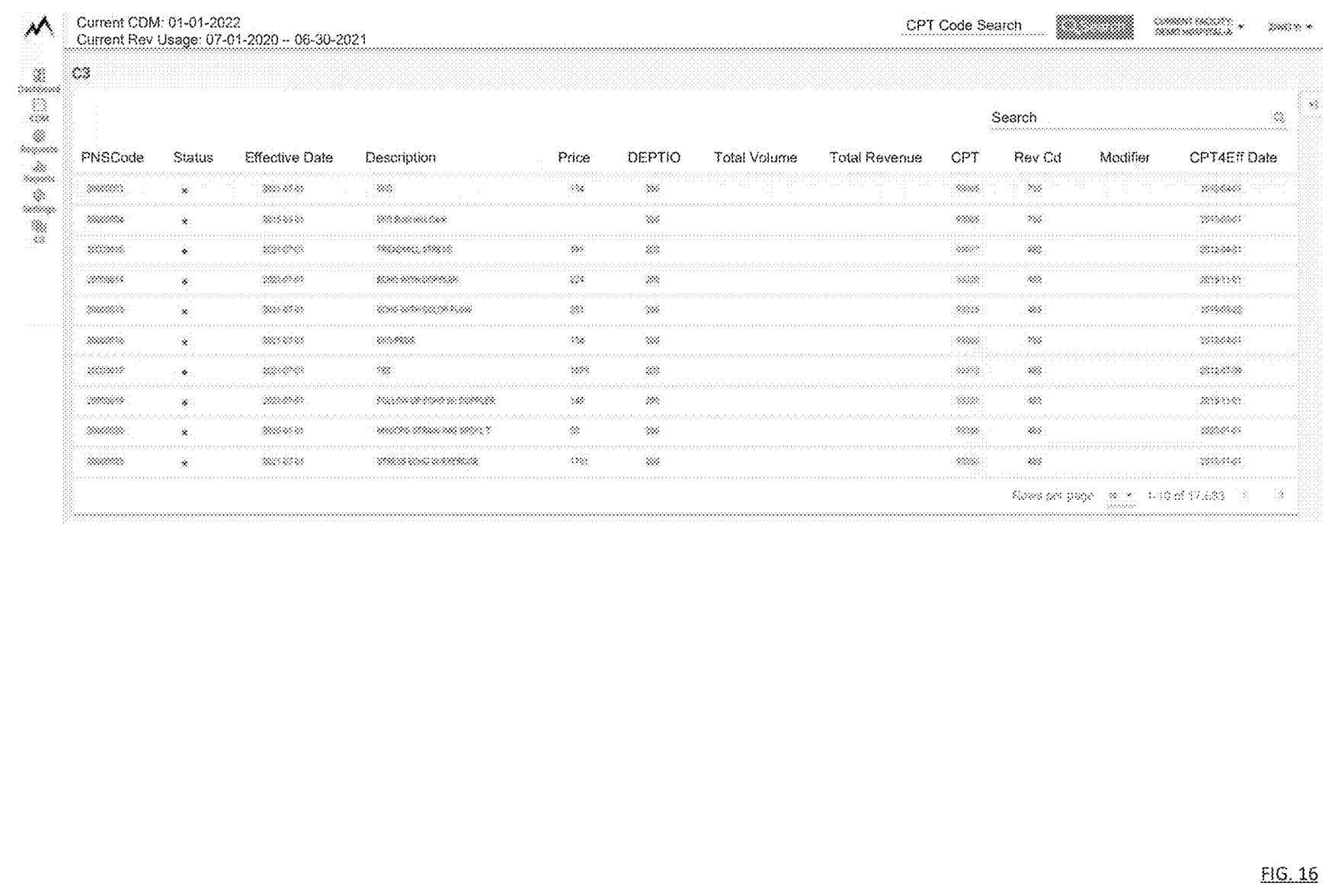
Figure 18:
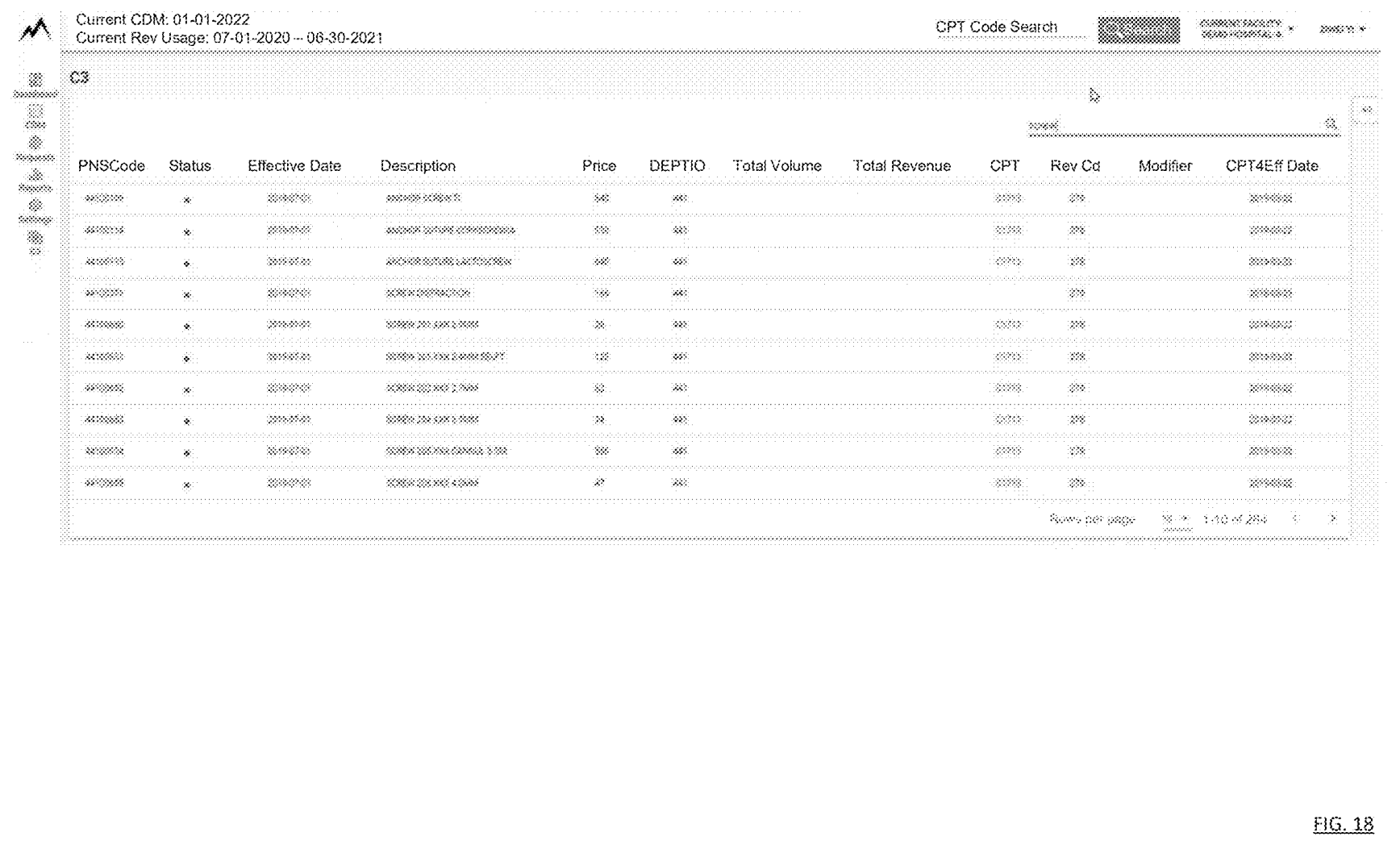
Figure 19:
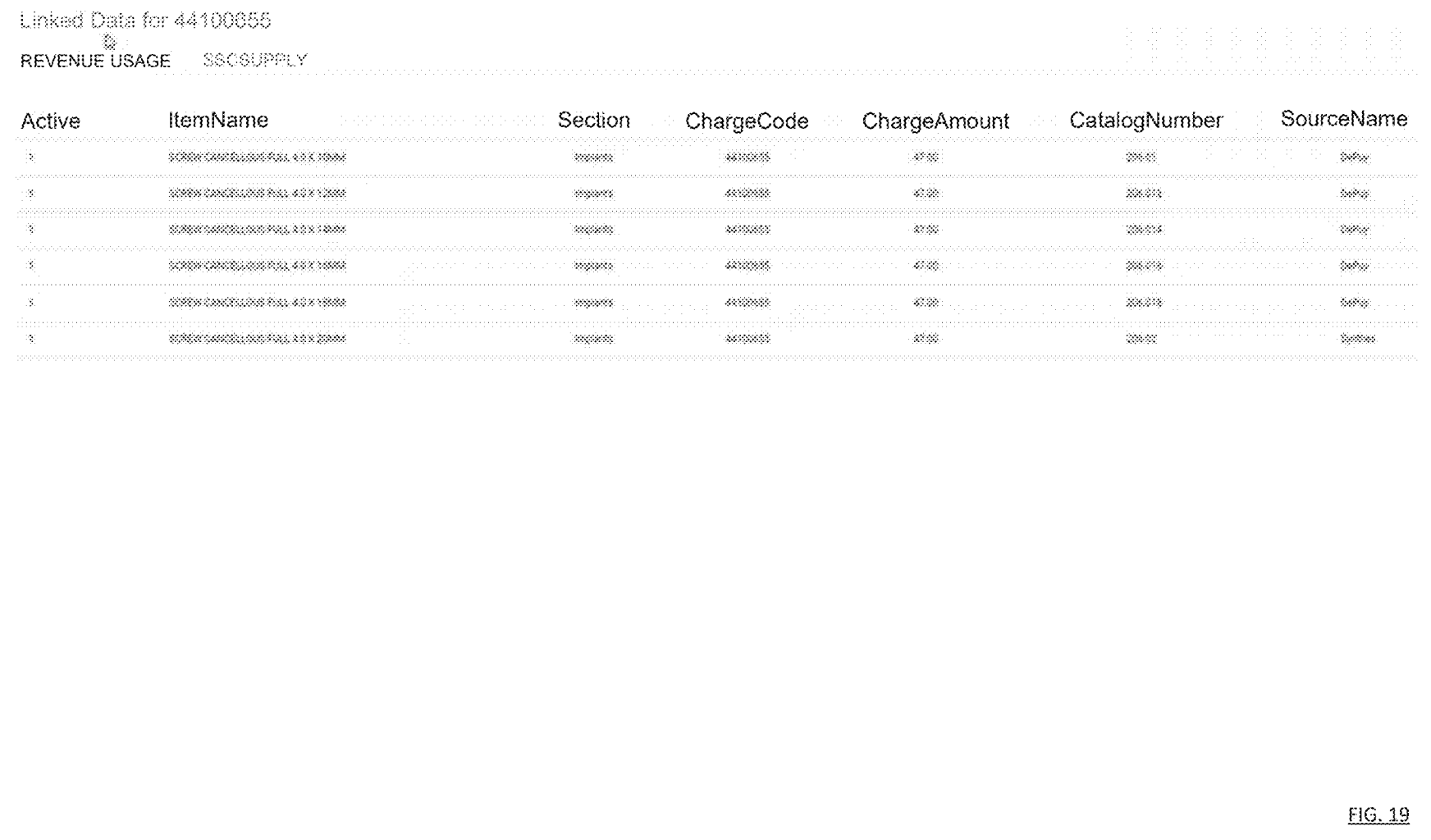

FIGS. 16 through 19 include screen displays demonstrating how various records linked to a CDM identification number can be displayed.

FIG. 20 is a screen display showing a reporting section of a navigator application configured for use in connection with a transaction analysis system.

FIG. 21 includes an example of an OE-not-mapped report.

FIG. 22 is a screen display illustrating examples of order entry line items that have been mapped to a CDM but which have issues.

FIG. 23 illustrates an example of a report of order entry items that appear to be mapped to a charge code but with charge codes which are considered invalid.

FIG. 24 shows an example of a report called OE-implants-mapped-to-non-implements-revenue-codes which can be generated in connection with an OR Supply module.

DESCRIPTION

Figure 1:
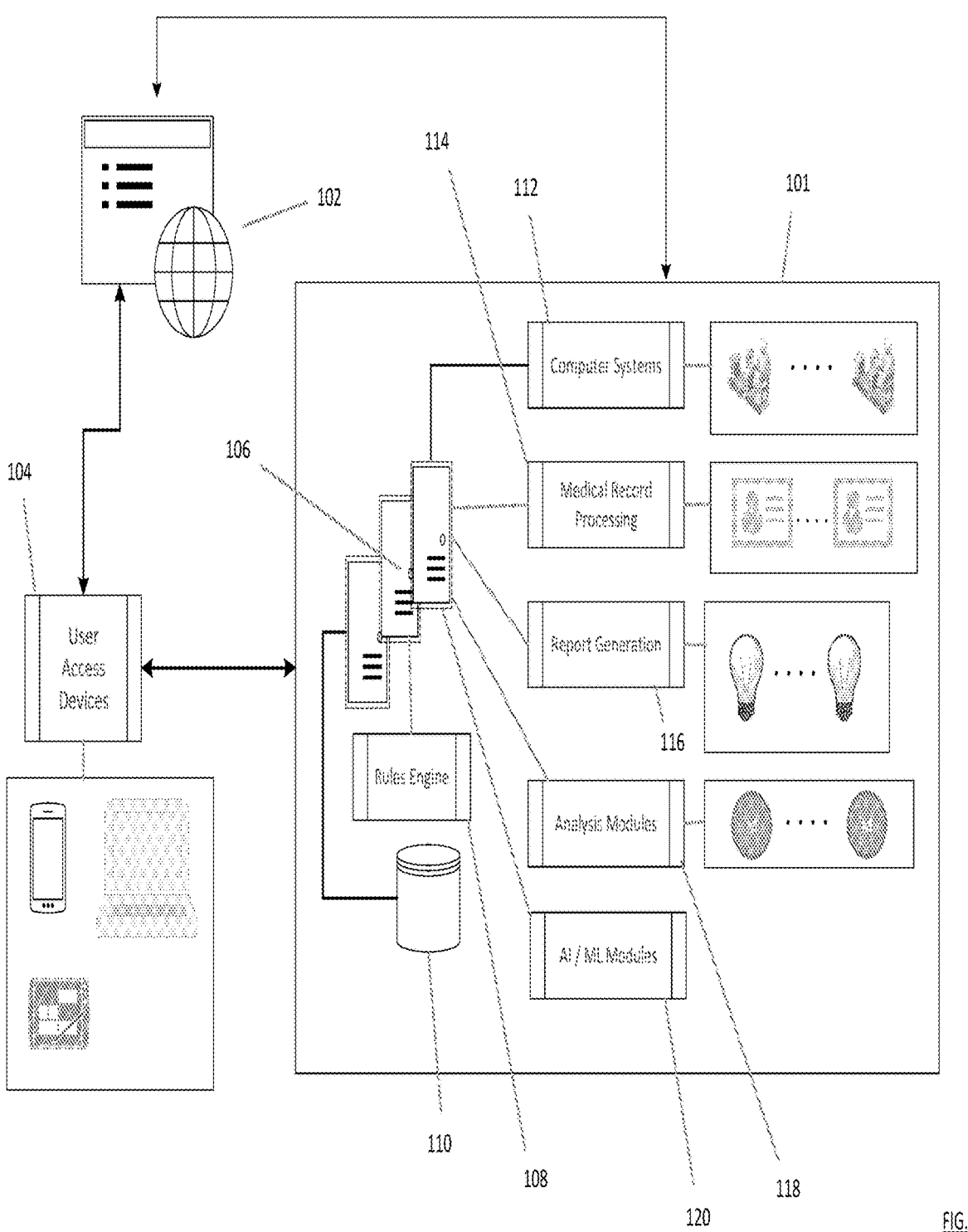
FIG. 1 schematically illustrates an example of a computing environment in which a transaction analysis system operates to analyze health care procedure related data.

In developing the various embodiments of the invention described herein, the inventors have appreciated the need for advanced technology for analyzing health care clinical treatment data and the financial transactions associated with such treatment.

Clinical services provided to patients are typically entered into specific software systems, Order Entry Systems, (OES) for a given clinical area, such as Cardiac Catheterizations, CT Scans or Laboratory testing. These IT systems are responsible for ordering the patient work, registering the clinical results and handing off the clinical charging data to the hospital or physicians finance IT system to subsequently be billed to the patient or patient's insurer. It is most critical that the charge data is accurately and efficiently transferred from the clinical area to the financial area for billing purposes. The core of the financial system for billing the clinical services or supplies charged to the patient is the use of a database termed the Charge Description Master (CDM). Hospitals and physicians use the CDM, to store descriptions of chargeable services and supplies as recognized specifically by Medicare and commercial payors.

The description of the service or supply is most critical for two purposes; first, the OES must adequately describe the service procedure or supply being provided: secondly the OES description must be close to or identical to the CDM: third, the unit of measure must be correctly reflective in OES and CDM. This function will be either performed in a manual effort or be provided by artificial intelligence software. Ultimately, the services or supplies must be aligned and compliantly used under Medicare regulations. Most hospitals and physician practices have independent computer-based clinical ordering systems that feed charges to the CDM based on a common linked code that connects the line items. These systems commonly remain independent of the facilities main frame based computer systems which houses the CDM. The services or supplies listed in an OES can be cross walked to the services and supplies listed in the CDM database.

The primary commonality between OES and the CDM line items are the description and unit of measure of the procedure, service or supply. Changes in the healthcare industry are incessant, consequently, changes occur from both the OES and the CDM. Population of line items among the OES and the CDM is an ongoing primary problem for healthcare. For example, a surgeon can introduce a new surgical procedure that previously did not exist in either the OES or CDM. A problem occurs when a surgical procedure is loaded in the OES but is not correspondingly loaded into the CDM. Consequently, the surgical service is ordered, provided, and the OES issues a charge, but the charge is not acknowledged nor received by the CDM. Consequently, the patient is not charged for the surgical service and the hospital is not correctly reimbursed for surgery.

In certain aspects of the environment, maintaining consistency for units of measure among the OES and CDM data items is another arduous task for hospital personnel. It is necessary to delve into both the OES and the CDM databases to ensure that the volume for the line item is correct and charged according to the insurers regulations or contracts. This problem exists most frequently in the supply area. Furthermore, it is normally the responsibility of the finance staff to dictate correct units of measure for a given supply. One example is where media contrast is billed by the milliliter but the OES is charging by the vial. The unit of measure from the OES will be 1 whereas it should be 150 ml, therefore understating the billing for contrast by 149 ml.

Active flags for both OES and CDM line items is a critical measure due to electronic connectivity on both sides. It is common that among the thousands of line items, that active flags get incorrectly set to in-active. When reviewing OES to CDM manually, the human eye will not see these flags. Therefore, while the line items might match according to descriptors and units of measure, either flag for the OES or CDM can be incorrect and the charge will not flow to the patient bill.

Chargeable flags for both OES and CDM line items is a critical measure due to electronic connectivity on both sides. It is common that among the thousands of line items, active flags are often incorrectly set to inactive. When reviewing OES to CDM manually, the human eye will not see these flags. Therefore, while the line items match according to descriptors and units of measure, when either flag for the OES or CDM is incorrect the charge will not flow to the patient bill.

In various embodiments, the present invention can include a system that reviews how OES chargeable data line items are to be matched to the chargemaster based on the crosswalk file for each clinical service area. The OES descriptors can be compared against the CDM descriptors, and the governing rule for the descriptor comes from Medicare. The Medicare descriptor is commonly inserted into the CDM verbatim, while the OES descriptor is commonly stated in a more clinical lay person terminology. It is assumed that clinical charges are to be mapped to a financial charge which is applied to a patient bill. Typically, there exist thousands of clinical charges throughout the facility. Correspondingly, the CDM houses thousands of financial charges. Therefore, a problem arises when the OES service being provided is not directly assigned to the actual service listed in the CDM. Another problem arises when Medicare or the AMA changes the regulatory descriptor, which is then changed in the CDM. For instance, if an intravenous (IV) therapy service that was charged by the day is now charged by the hour, both the OES and CDM must be adjusted to charge for each hour of service. This requires the CDM finance staff to allow for a per hour charge with a corresponding price change. The OES clinical staff can change the OES descriptor and alert the clinicians of such a change. Many times, however, this type of change is corrected in the CDM but not changed in the OES. Therefore, the volume of hours that are actually used will be charged only as a volume of one. In various embodiments, the system can flag the error before any under billing might occur.

In various embodiments, a computer-implemented method can be configured for analyzing health care procedure related transactions of a health care entity. The method may include importing, by a transaction analysis computer system including at least one electronic computer processor and at least one of the computer-readable medium, at least the following information: at least a portion of a charge description master (CDM) file containing multiple CDM data items, at least a portion of an order entry system (OES) file containing multiple OES data items, and at least a portion of a CDM-to-OES cross-reference data file. The method may further include creating, by the transaction analysis system applying the CDM-to-OES cross-reference data file to the CDM data items file and the OES data items file, a linked data items file. The method can include analyzing, by the transaction analysis system, the linked data items file, wherein the analyzing comprises reading at least one linked line item of the linked data items file, analyzing a CDM data portion of the linked line item, analyzing an OES data portion of the linked line item, and comparing the linked CDM data portion to the linked OES data portion of the linked line item for determining at least one similarity or difference between the CDM data portion and the OES data portion.

The method may further comprise analyzing the CDM data portion of the linked line item for determining an active or inactive status of a CDM data item, and/or analyzing the CDM data portion of the linked line item for determining a chargeability status of a CDM data item. Likewise, the OES data portion of the linked line item can be analyzed for determining an active or inactive status of an OES data item, and/or the OES data portion of the linked line item can be analyzed for determining a chargeability status of an OES data item. Instead of conducting the analysis in the direction of comparing the CDM data portion to the OES data portion, the method may involve cdm ing the linked OES data portion to the linked CDM data portion of the linked line item for determining at least one similarity or difference between the OES data portion and the CDM data portion. In certain embodiments, the analysis may be conducted in one or both directions and in any sequential order desired.

The method may involve determining at least one similarity or difference between the CDM data portion and the OES data portion by comparing at least a portion of a description associated with the CDM data portion to at least a portion of a description associated with the OES data portion. The method may involve determining at least one similarity or difference between the CDM data portion and the OES data portion by comparing at least a portion of a unit of measure associated with the CDM data portion to at least a portion of a unit of measure associated with the OES data portion.

In other aspects, the method may comprise identifying at least one OES data item unmapped to any CDM data item, determining an active or inactive status of the unmapped OES data item, and/or determining a chargeability status of the unmapped OES data item. The method may comprise identifying at least one CDM data item unmapped to any OES data item, determining an active or inactive status of the unmapped CDM data item, and/or determining a charge-ability status of the unmapped CDM data item.

In various embodiments, the method may implement an artificial intelligence module for analyzing the CDM data portion of the linked line item, for analyzing the OES data portion of the linked line item, for comparing the CDM data portion to the OES data portion of the linked line item for determining at least one similarity or difference between the CDM data portion and the OES data portion, and/or for comparing the OES data portion to the CDM data portion of the linked line item for determining at least one similarity or difference between the OES data portion and the CDM data portion.

The method may further comprise communicating at least one electronic mail notification in response to determining at least one similarity or difference between the OES data portion and the CDM data portion.

Figure 2:
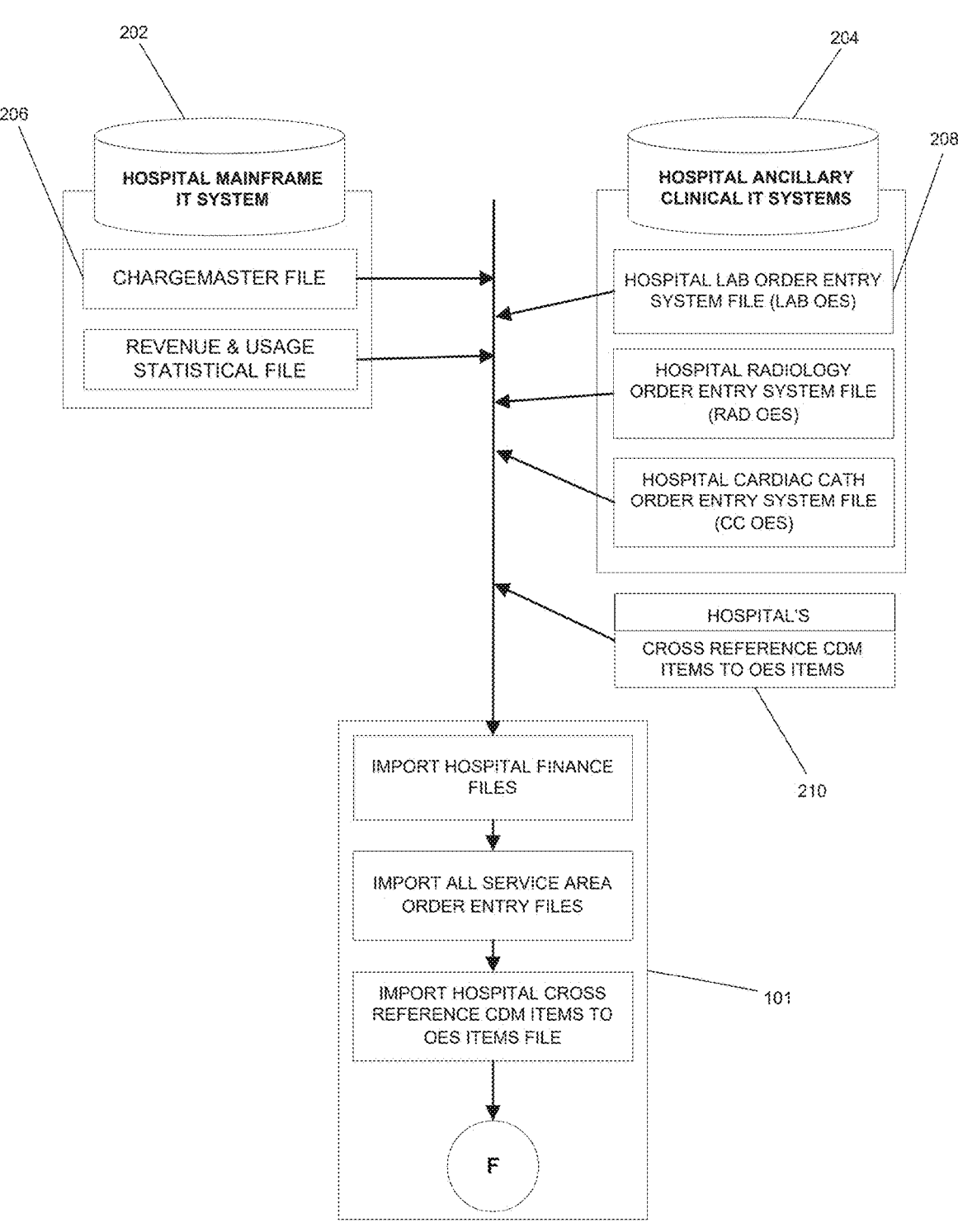
FIG. 2 is a process flow diagram illustrating examples of processes for performing the collection or aggregation of data from multiple sources.

FIGS. 1 and 2 schematically illustrate an example of a computing environment and associated process flows in which a transaction analysis system 101 operates to analyze data associated with the health care procedure related trans-actions of a health care entity (e.g., a hospital or other health care facility). The system 101 can be accessed via a variety of communication media (e.g., wireless communication, hardwired connection, Internet, intranet, browser software, or others) by various types of access devices 104 (e.g., laptops, servers, mobile devices, notebooks, or other types of computing devices or computer systems). The analysis system 101 may include one or more electronic computer-based processors 106 (e.g., servers) configured to execute various tasks, perhaps in conjunction with a rules engine module 108, for example. One or more electronic data storage media or memory media 110 can be configured for operative association with the processor 106 and configured for performing data storage, access, or retrieval operations conducted by the system 101.

In certain embodiments, the system 101 may include one or more computer system modules 112 for interfacing with one or more external computer systems associated with a health care facility, for example, such as a mainframe system 202 and/or one or more ancillary clinical systems 204 of a hospital. A medical record processing module 114 can be configured to process data associated with CDM data files 206, OES data files 208, and/or a CDM-to-OES cross-reference file 210, as shown in this example. In other aspects, a report generation module 116 can be configured to generate various kinds of reports associated with the analy-sis performed by various analysis modules 118 of the system 101 (the functions of the analysis modules 118 are described in more detail below). In other aspects, one or more artificial intelligence and/or machine learning modules 120 can be configured to automate and execute more efficiently the various analysis tasks described herein.

FIG. 2 is a process flow diagram illustrating examples of processes for performing the collection or aggregation of data from multiple sources. As shown, the transaction analy-sis system 101 can be configured to import from the hospital mainframe computer system 202, the CDM data file 206 and/or associated revenue and usage statistical data related to the volume charged and payors (e.g., insurance firm) for various medical procedures. The analysis system 101 can import clinical data derived from the OES data file 208. The hospital's cross-reference file 210 can also be imported to provide information regarding the then existing connectivity between the CDM data items and the applicable OES data items. All or a portion of this collected data may be collected and aggregated into a clinical to financial charging model created in the analysis system 101. For example, clinical charges that have been mapped to financial charges can be used in certain aspects of the analysis. The CDM population of chargeable data item lines may each include a descriptor, a CPT code, revenue code, modifier, and/or a unit price, among other data fields. A clinical order entry data item line may be comprised of a clinical descriptor and an identifying number. Various embodiments of the invention have the ability to generate different types of reports that illustrate mapping of the CDM charge and the OES charge on a one-to-one basis.

Figure 3:
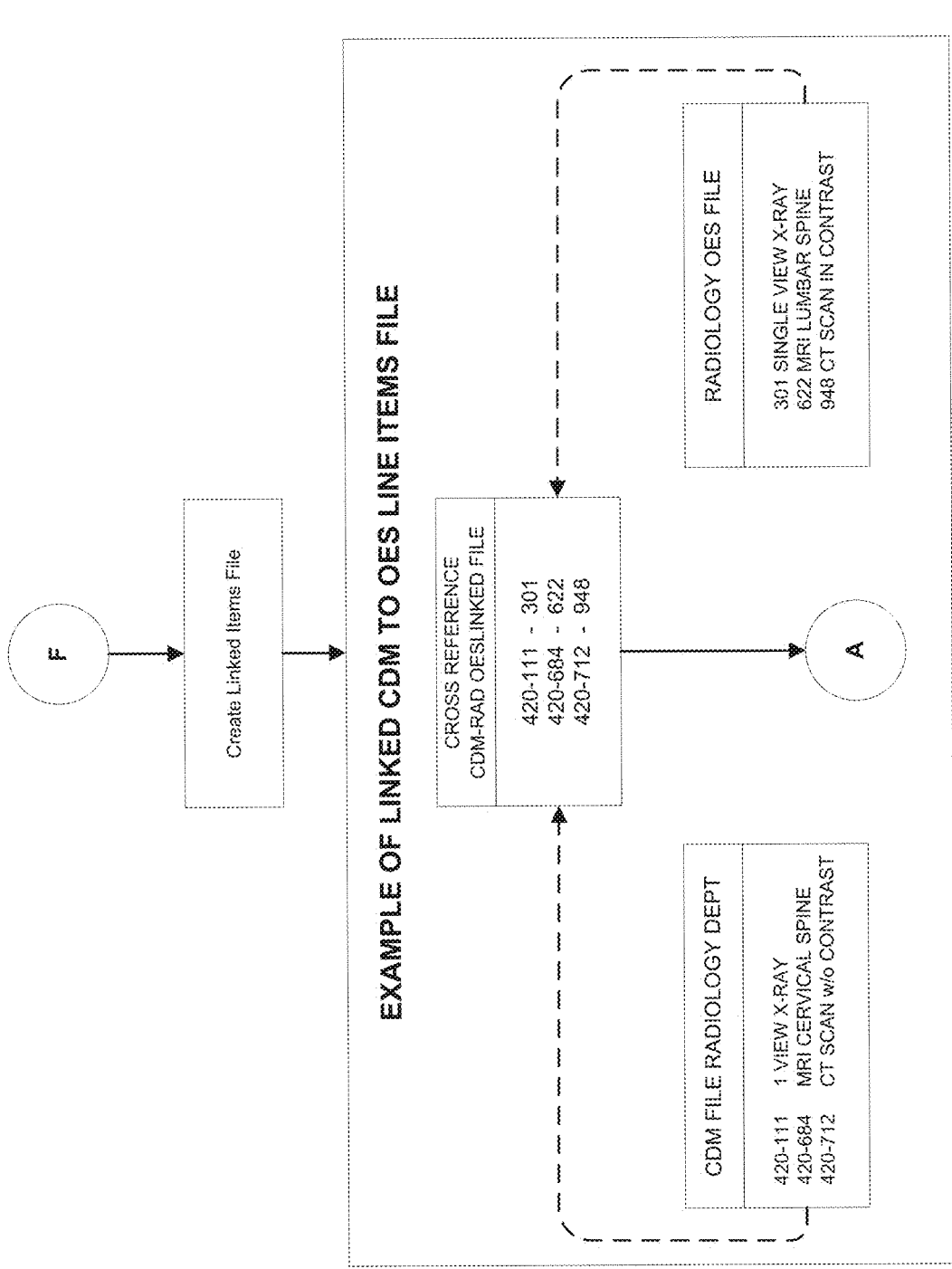
FIG. 3 includes a process flow diagram illustrating an example of creating a linked data item file.

FIG. 3 includes a process flow diagram illustrating an example of creating a file of the line items that are identified by a common linked number and is formatted and listed in numeric order by CDM number. This is performed by using the cross reference CDM to OES items data file, which provides the linkage file of the OES line items and CDM line items as they currently exist in the system. FIG. 3 illustrates an example of a CDM file with three radiology line item procedures as they are mapped to the OES line item file. A unique item number for a 1 View X-Ray from the CDM to a Single View X-Ray from the OES provides the electronic means of charges flowing from the OES to the CDM. Using this linked CDM and OES line items file facilitates the step of examining only the line items that are linked.

Figure 4:
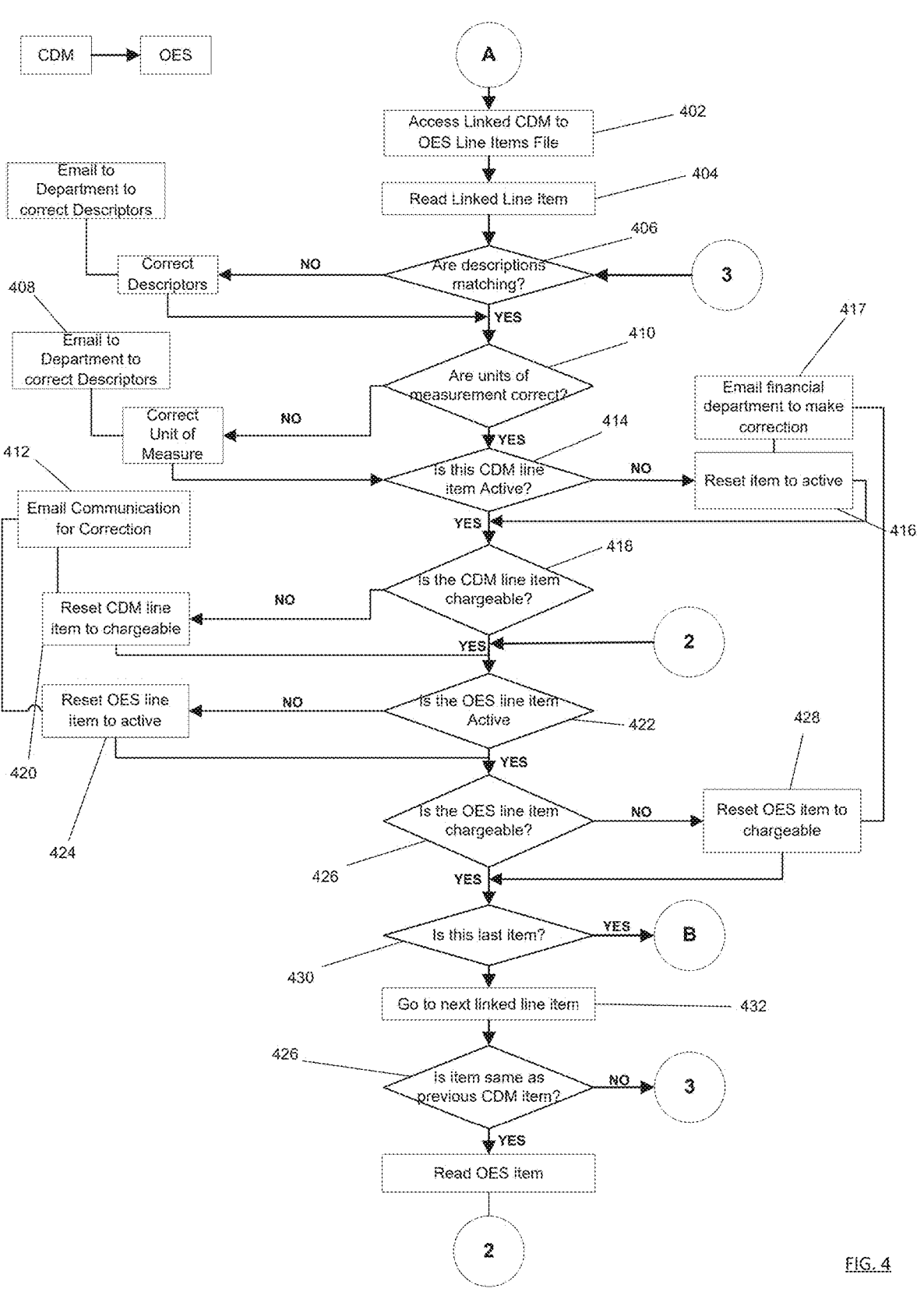
FIG. 4 includes a process flow diagram illustrating an example of comparing charge description master (CDM) data items to order entry system (OES) data items.

FIG. 4 includes a process flow diagram illustrating an example of analyzing the CDM data items to the OES data items that are currently linked from the mapped CDM and OES items cross-reference file 210. After accessing the cross-reference file at step 402, the process reads a linked data item at step 404. The process can then determine at step 406 whether the descriptions are matching, which can be accomplished via either an artificial intelligence software algorithm or manual effort, or a combination thereof. If a discrepancy exists in either the OES data item or the CDM data item, then the analysis system 101 can automatically communicate an e-mail at step 408, for example, to prede-termined clinical and financial staff regarding the discrep-ancy and what needs to be corrected, thus creating a docu-mented audit trail of changes to be implemented. Another part of the process at step 410 can determine if the Unit of Measure (UOM) is correct in a comparison between the CDM and the OES data items. If a discrepancy exists in either the OES or CDM, then the analysis system can automatically communicate an e-mail at step 412 to prede-termined clinical and financial staff regarding the discrep-ancy and what needs to be corrected.

The process can then determine at step 414 based on a digital flag setting, for example, whether or not the CDM data line item is active or inactive. If it is set to inactive it can be set to active at step 416. Then the analysis system 101 can automatically communicate an e-mail at step 417, for example, to predetermined clinical and financial staff regarding the discrepancy and what needs to be corrected. The process can also determine at step 418 based on the flag setting whether or not the CDM data line item is chargeable or non-chargeable. If it is set to non-chargeable it can be reset to chargeable at step 420. The process can then determine whether or not the OES data line item is active or inactive at step 422. If it is set to inactive it can be reset to active at step 424. The process can then determine at step 426 based on the flag setting whether or not the OES line item is chargeable or non-chargeable. If it is set to non-chargeable it can be reset to chargeable at step 428. If it is determined that the current data item is the last data line item at step 430, then the processing can be directed to "B" (see FIG. 5). Otherwise, the process then reads the next data line item at step 432. If the CDM number is determined at step 434 to be not identical to the prior CDM number, then the processing steps can be directed to "3" as indicated in FIG. 4. Otherwise, if the CDM number is determined at step 434 to be identical to the prior CDM number, then the processing steps can be directed to "2" to read OES data items.

Figure 5:
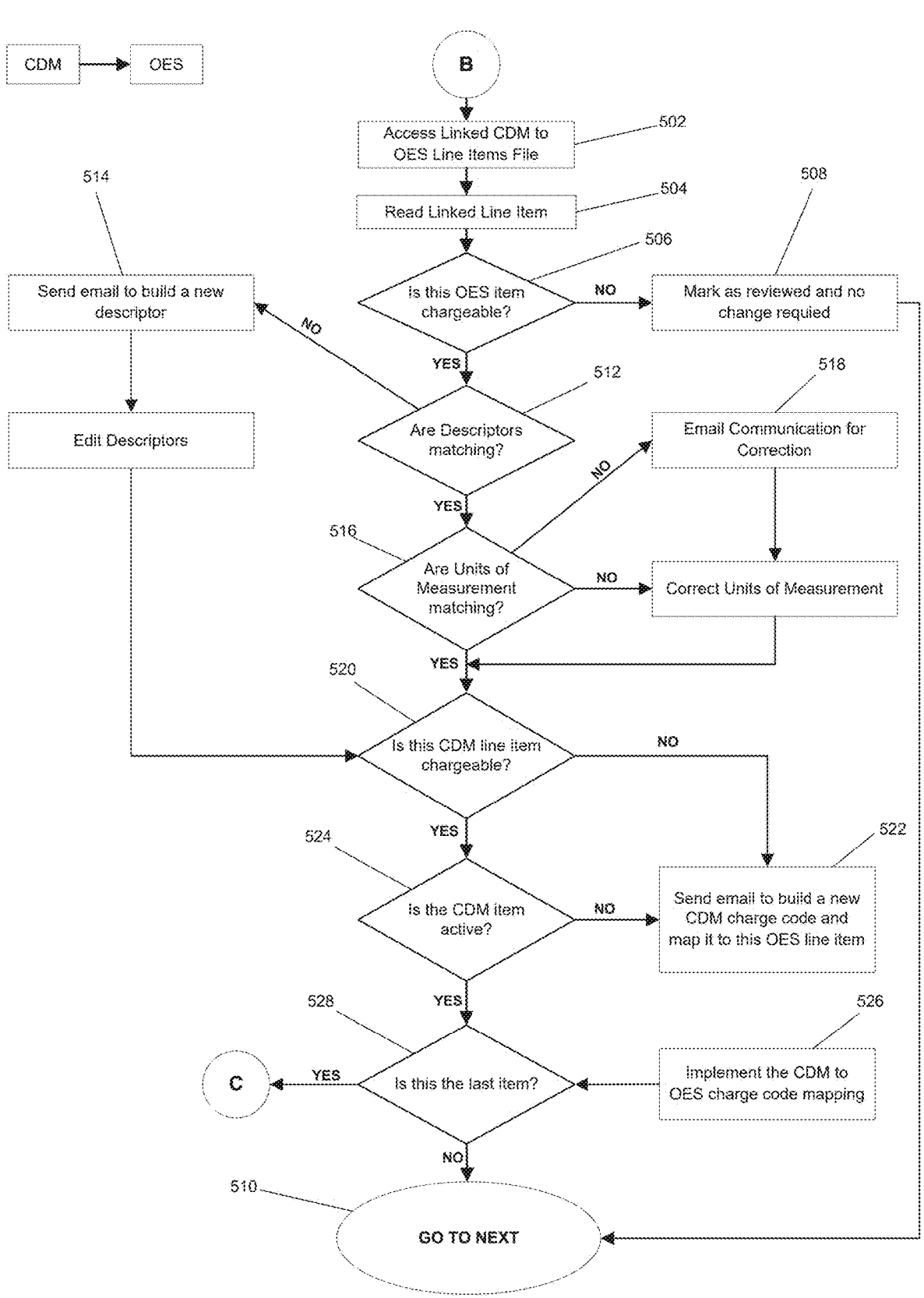
FIG. 5 includes a process flow diagram illustrating an example of analyzing OES data items to CDM data items.

FIG. 5 includes a process flow diagram illustrating an example of analyzing the OES data items currently mapped or cross-referenced as linked CDM and OES data items. As noted above, this cross-reference file 210 can be listed in CDM numerical order, for example. At step 502, the process can involve accessing the linked CDM-to-OES data line items file 210 and read each linked data item at step 504. The process can then determine at step 506 based on a flag setting, for example, whether or not the OES line item is chargeable or non-chargeable. If it is set to non-chargeable, it can be marked as reviewed and no change required at step 508, and then proceed to the next data item at step 510. The process can then determine at step 512 if the descriptions match via either an artificial intelligence software algorithm, manual review, or a combination thereof. If a discrepancy exists in either the OES data item or the CDM data item, then the analysis system 101 can automatically communicate an e-mail at step 514 to predetermined staff regarding the discrepancy and what needs to be corrected, thus creating a documented audit trail of changes. The process can determine at step 516 if the Unit of Measure (UOM) is correct between the CDM data item and the OES data item. If a discrepancy exists in either data item, then the analysis system 101 can automatically communicate an e-mail at step 518, for example, to predetermined staff regarding the discrepancy and what needs to be corrected. The process can also determine at step 520 based on the flag setting whether or not the CDM data item is chargeable or non-chargeable. If it is set to non-chargeable, then a new CDM line item can be built by the system 101 at step 522. Further analysis at step 524 determines based on the flag setting whether or not the CDM line item is active or non-active. If it is set to inactive, then the system can build a new CDM line item at step 522. Processing at step 526 can implement the newly built OES data item to CDM data item linkage into the cross reference CDM to OES item file 210. After the last data item has been processed (as determined at step 528), processing can proceed to "C" as indicated in FIG. 5.

Figure 6:
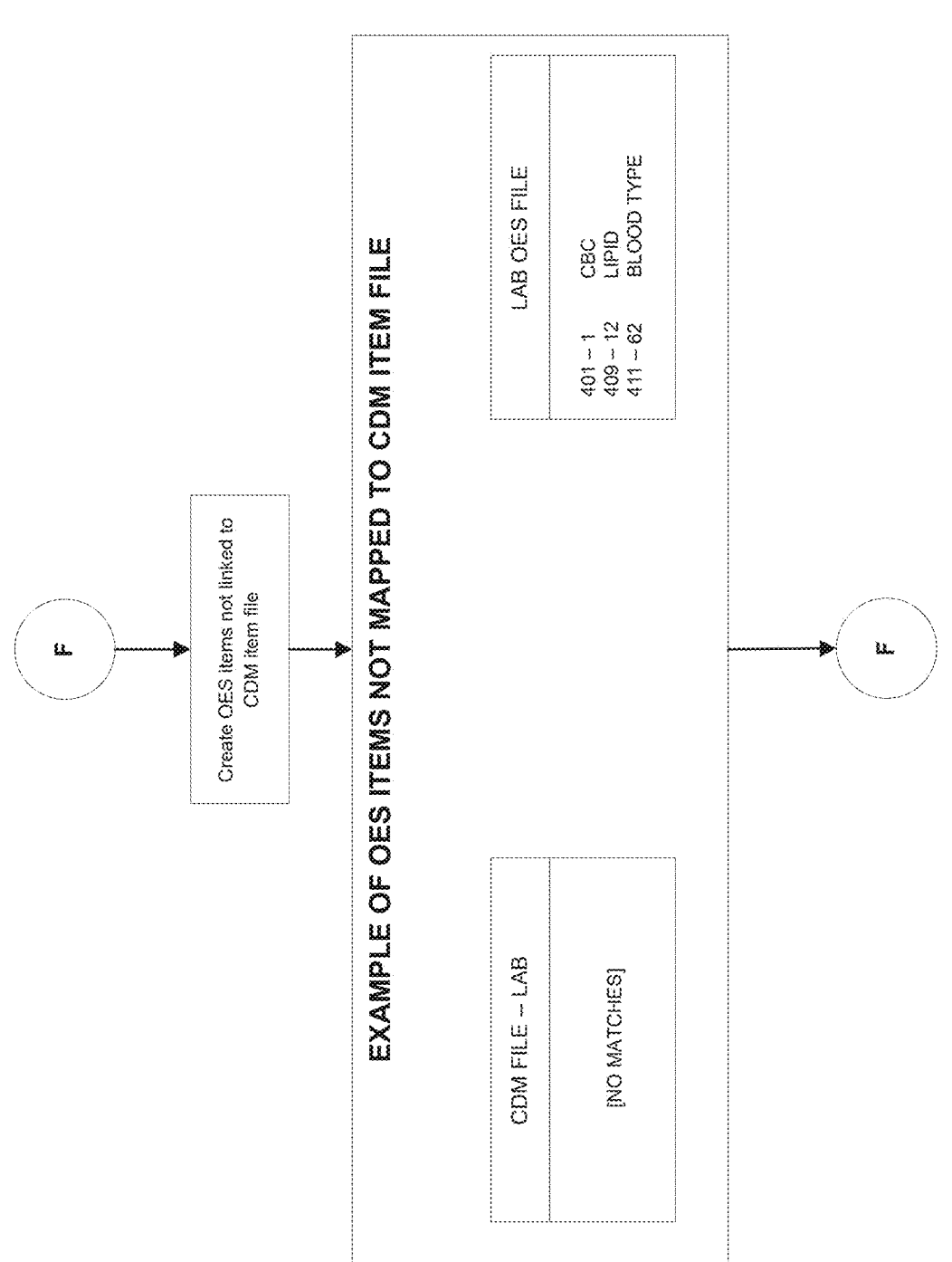
FIG. 6 includes a process flow diagram illustrating an example of creating a file for the OES data items that are not linked to CDM data items.

FIG. 6 includes a process flow diagram illustrating an example of the analysis system 101 creating a file for the OES data items that are not linked to CDM data items. This can be performed by using the cross-reference CDM to OES data items file 210. In this example, an OES file has three laboratory line item procedures that have no CDM line item linked to the laboratory items. The lack of having a CDM line item linked to these laboratory items is an example of lab services being performed, but there are no charges to be billed by a corresponding CDM line item.

Figure 7:
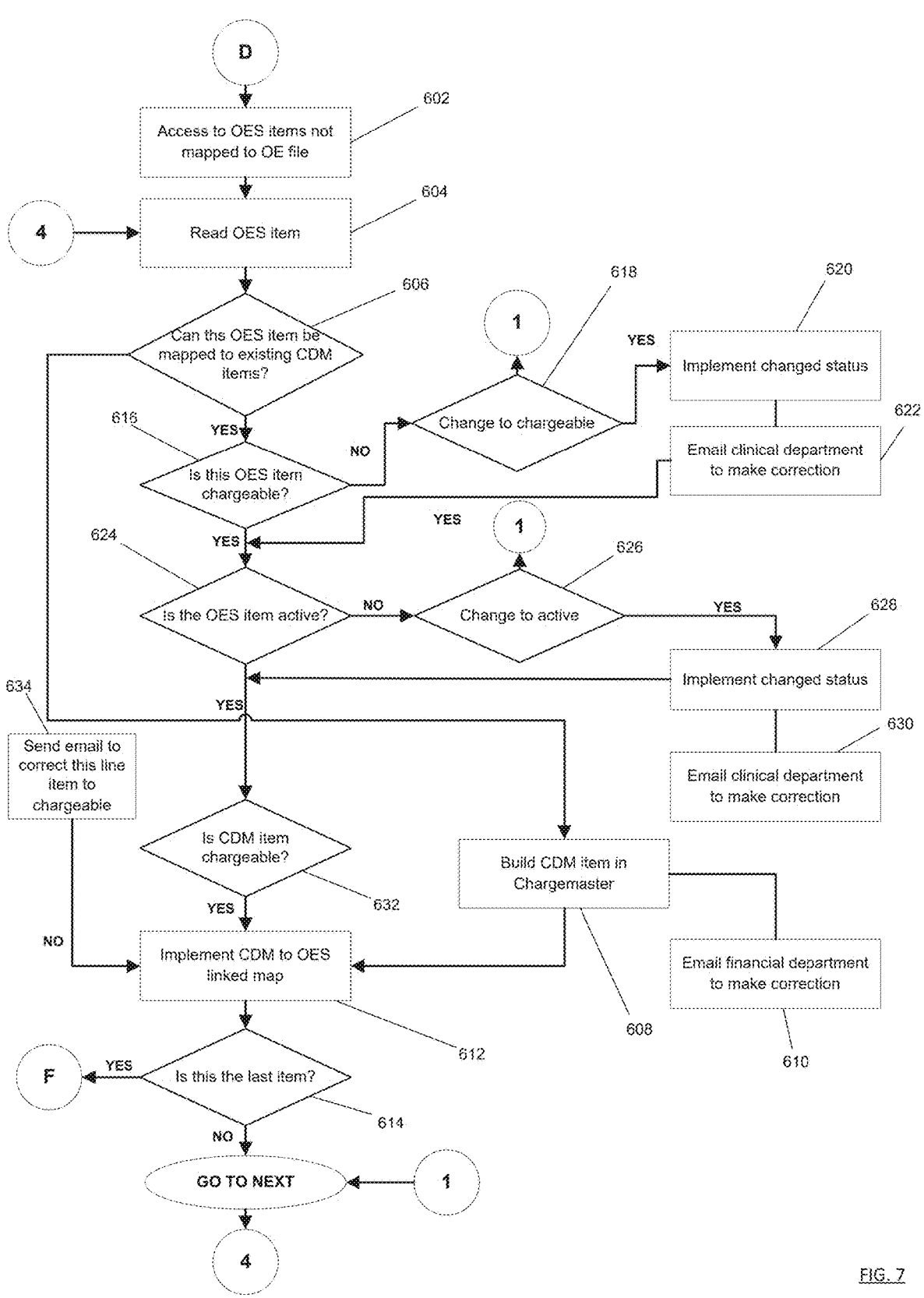
FIG. 7 includes a process flow diagram illustrating an example of determining if OES data items should be linked to CDM data items.

FIG. 7 includes a process flow diagram illustrating an example of determining if OES data items should be linked to CDM data items. At step 602, initial processing accesses the OES data items not mapped to the OES data file. Processing at step 604 reads each OES data item not linked to a CDM data item. The process then determines at step 606 if the OES data item can be mapped to an existing CDM data item. If it cannot be linked to an existing line item, then a CDM data item can be built at step 608. An e-mail can be automatically generated and communicated at step 610 to the appropriate clinical and financial staff to make and acknowledge the corrections. At step 612, changes can be implemented to the cross-reference file 210 based on the newly built CDM data item. At step 614, a determination can be made as to whether the last data item has been processed. If the last data item has been processed, then processing by the system 101 can proceed to "P" as indicated in FIG. 7; otherwise, processing can proceed to "4" to analyze the next data item at step 604.

At step 616, the process can determine based on a flag setting whether or not the OES line item is chargeable or non-chargeable. If the flag is set to non-chargeable, a determination can be made at step 618 whether it should be reset to chargeable, and then processing can proceed to "1" (and on to the next OES data item). If it is determined that the OES data item should be change to chargeable that changed status can be implemented at step 620. An email can be automatically generated and communicated at step 622 to the appropriate clinical and financial staff to make and acknowledge the corrections.

At step 624, processing step can determine based on the flag setting whether or not the OES data item is active or inactive. If it is set to inactive, a determination can be made whether it should be reset to active at step 626, otherwise processing can proceed to the next OES data item. At step 628, the changed status can be implemented, and at step 630 an e-mail can be automatically generated and communicated to the appropriate clinical and financial staff to make and acknowledge the corrections. The process can determine at step 632 based on the flag setting whether or not the CDM line item is chargeable or non-chargeable. If it is set to non-chargeable it can be reset to chargeable at step 634, and an e-mail can be automatically generated and communicated to appropriate clinical and financial staff to make and acknowledge the corrections. The new line item linkage can be implemented at step 612 to the cross reference CDM items to OES items file 210. Upon conclusion of processing the relevant data items, further processing of unmapped data items can proceed at "P" (see FIG. 8).

Figure 8:
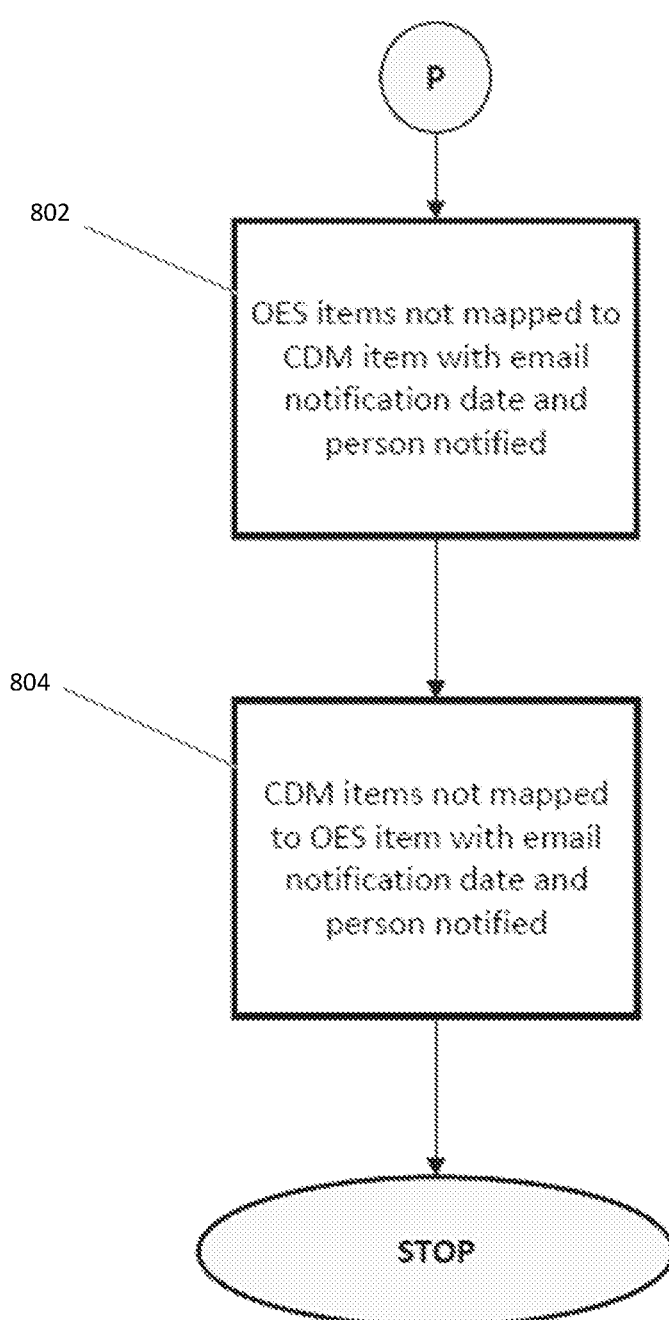
FIG. 8 includes a process flow diagram illustrating an example of processing unmapped data items.

FIG. 8 includes a process flow diagram illustrating an example of processing unmapped data items. At step 802, OES data items not mapped to CDM data items can be communicated for implementation of appropriate changes. At step 804, CDM data items not mapped to OES data items can be communicated for implementation of appropriate changes.

Figure 9A:
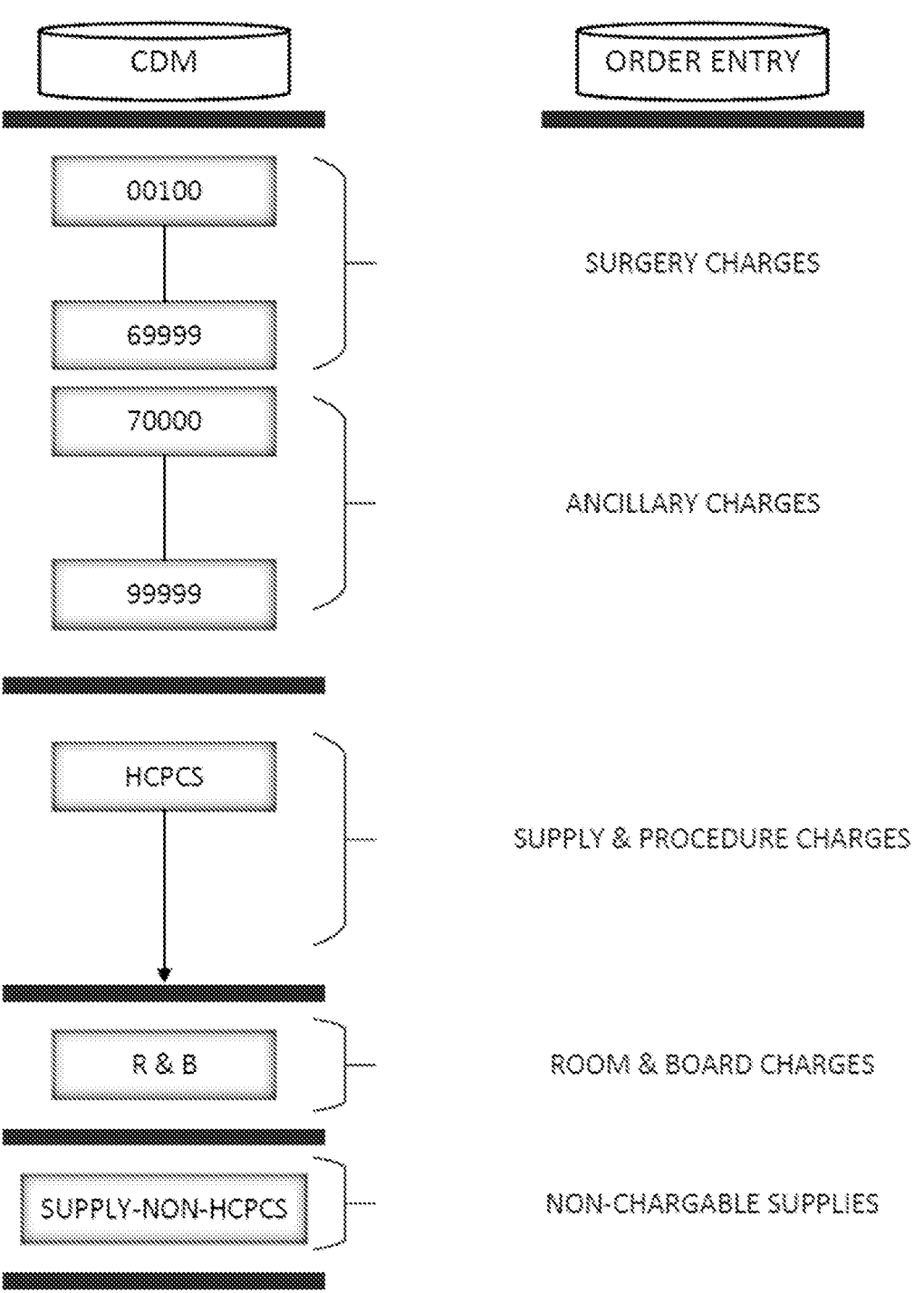
FIG. 9A schematically illustrates examples of mapping CDM data items to OES data items.
Figure 9B:
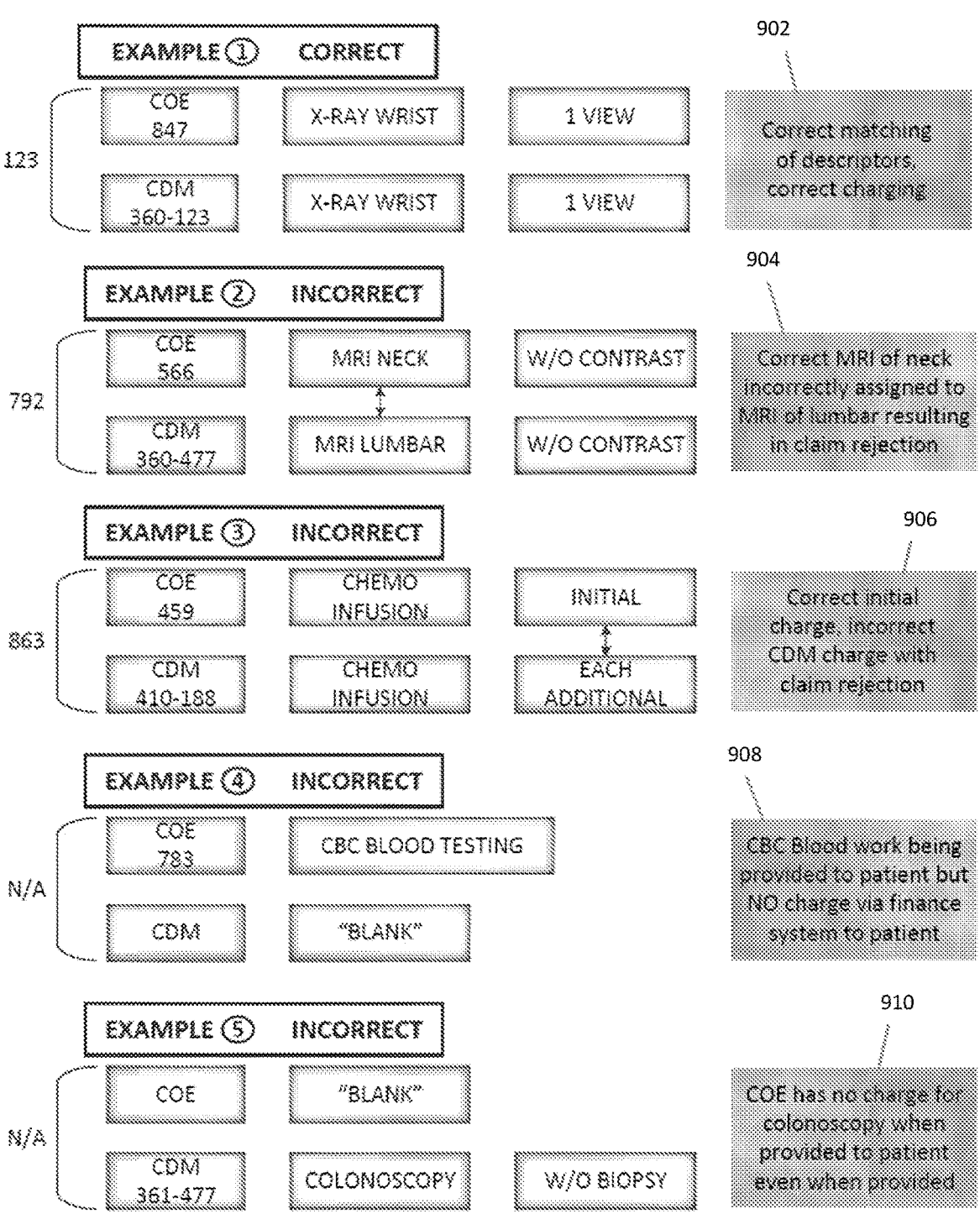
FIG. 9B schematically illustrates various specific examples of the results of the analysis performed by the transaction analysis system.

FIG. 9A schematically illustrates examples of mapping CDM data items to OES data items. FIG. 9B schematically illustrates various specific examples of the results of the analysis performed by the transaction analysis system. Example 902 illustrates correct matching of descriptions with correct charging. Example 904 shows a correct MRI of a neck incorrectly assigned to an MRI of a lumbar spine section. Example 906 demonstrates a correct initial charge, but an incorrect CDM charge resulting in a claim rejection. Example 908 illustrates CBC blood work being provided to a patient, but no resulting charge to the patient. Example 910 shows how the OES (or cost order entry (COE) system) has no charge for a colonoscopy performed as a medical procedure for a patient.

FIGS. 10 through 24 illustrate certain aspects of the operation and function of one example of a navigator software application (sometimes referred to herein as "CDM navigator") as implemented in operative association with one example of a transaction analysis system.

Figure 10:
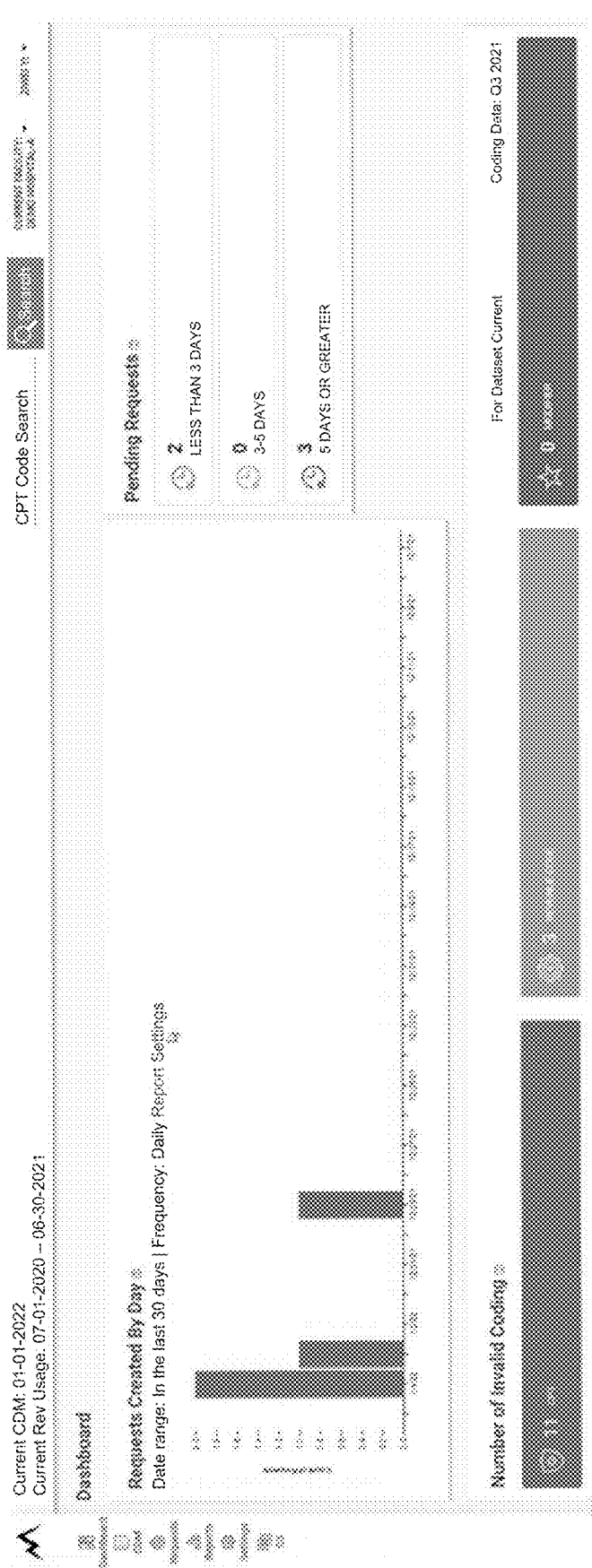
FIG. 10 is a screen display illustrating an example of a dashboard view of navigator application configured for use in connection with a transaction analysis system.
Figure 11:
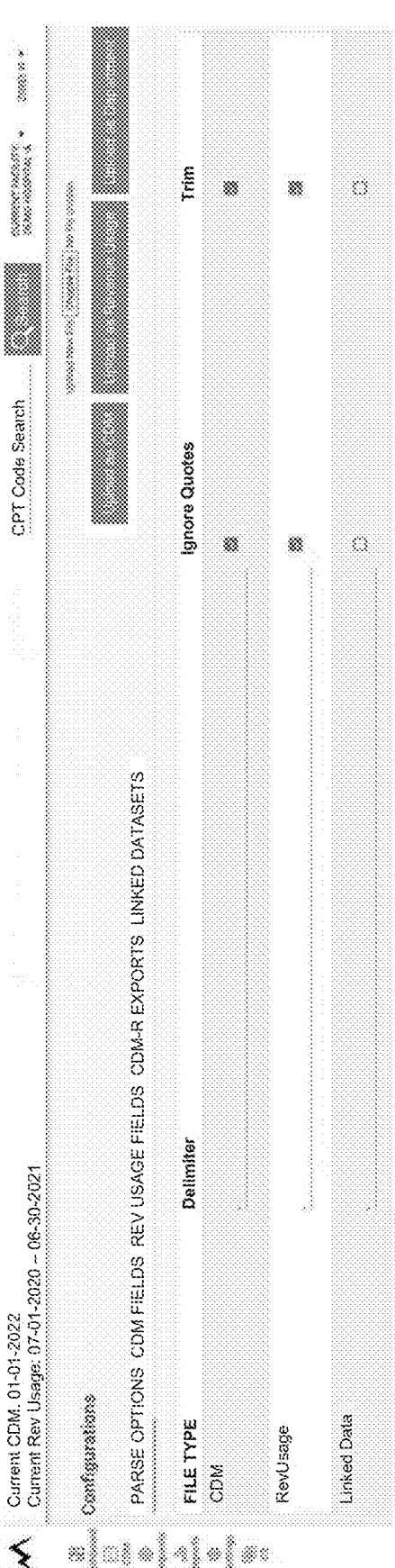
Figure 12:
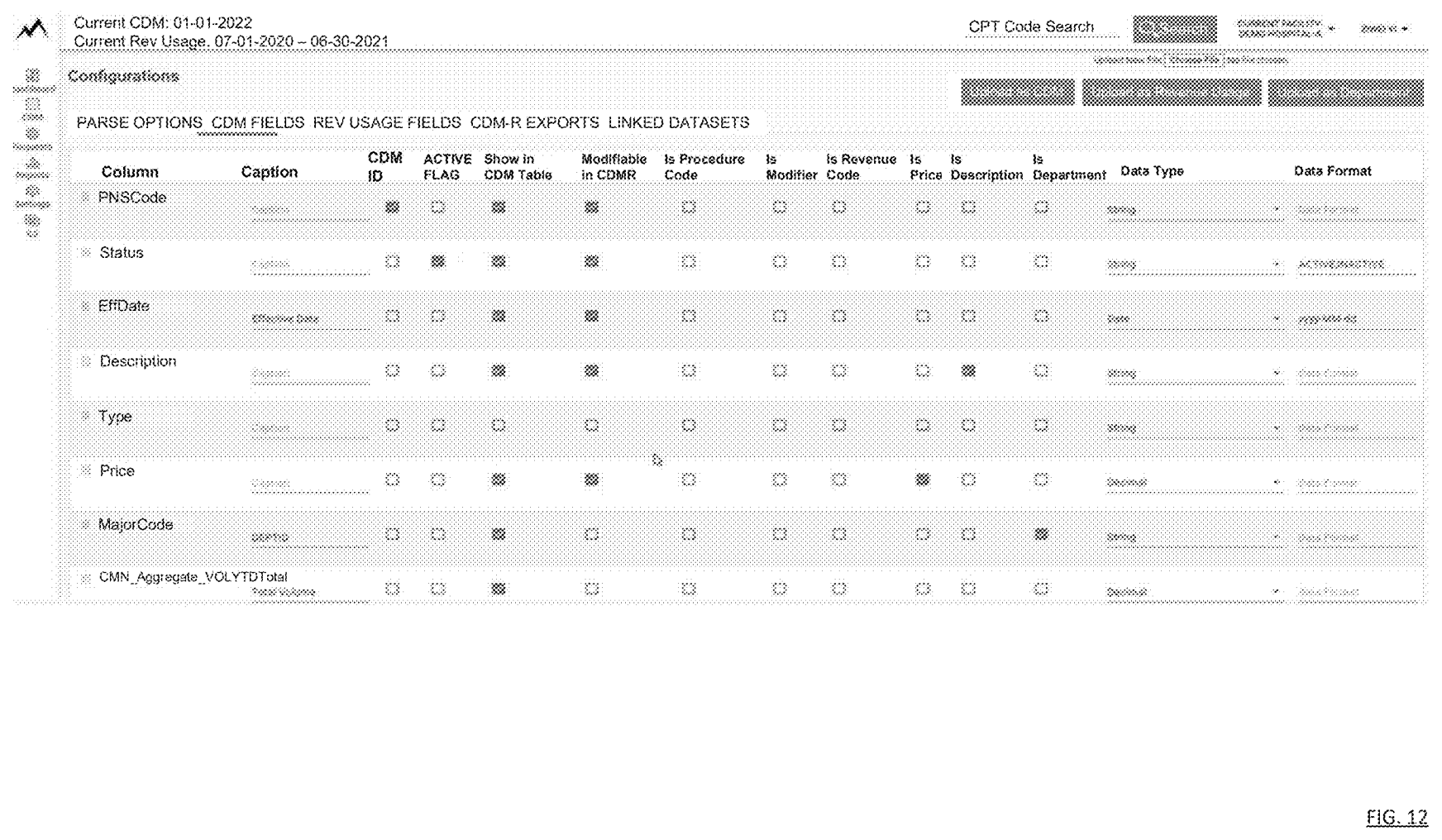
Figure 13:
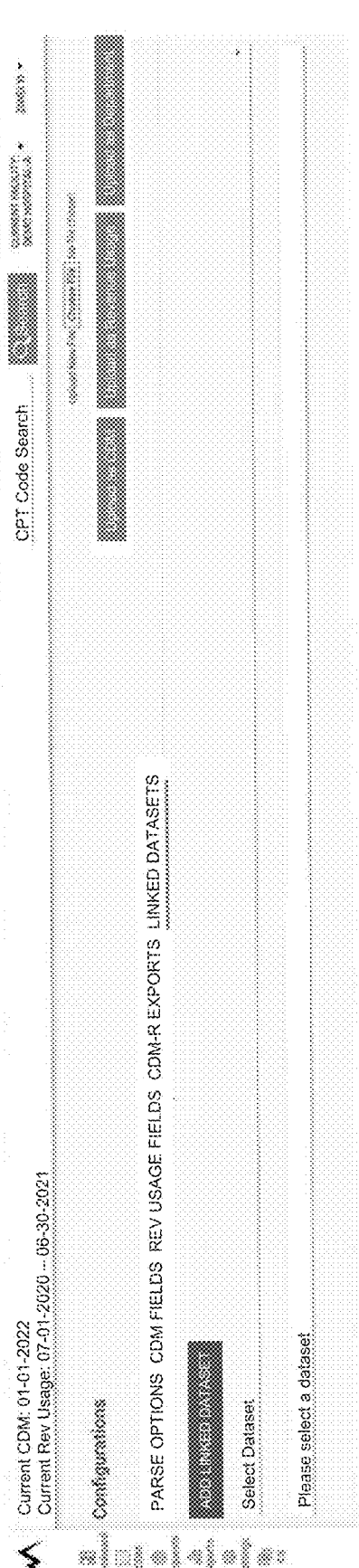
Figure 14:
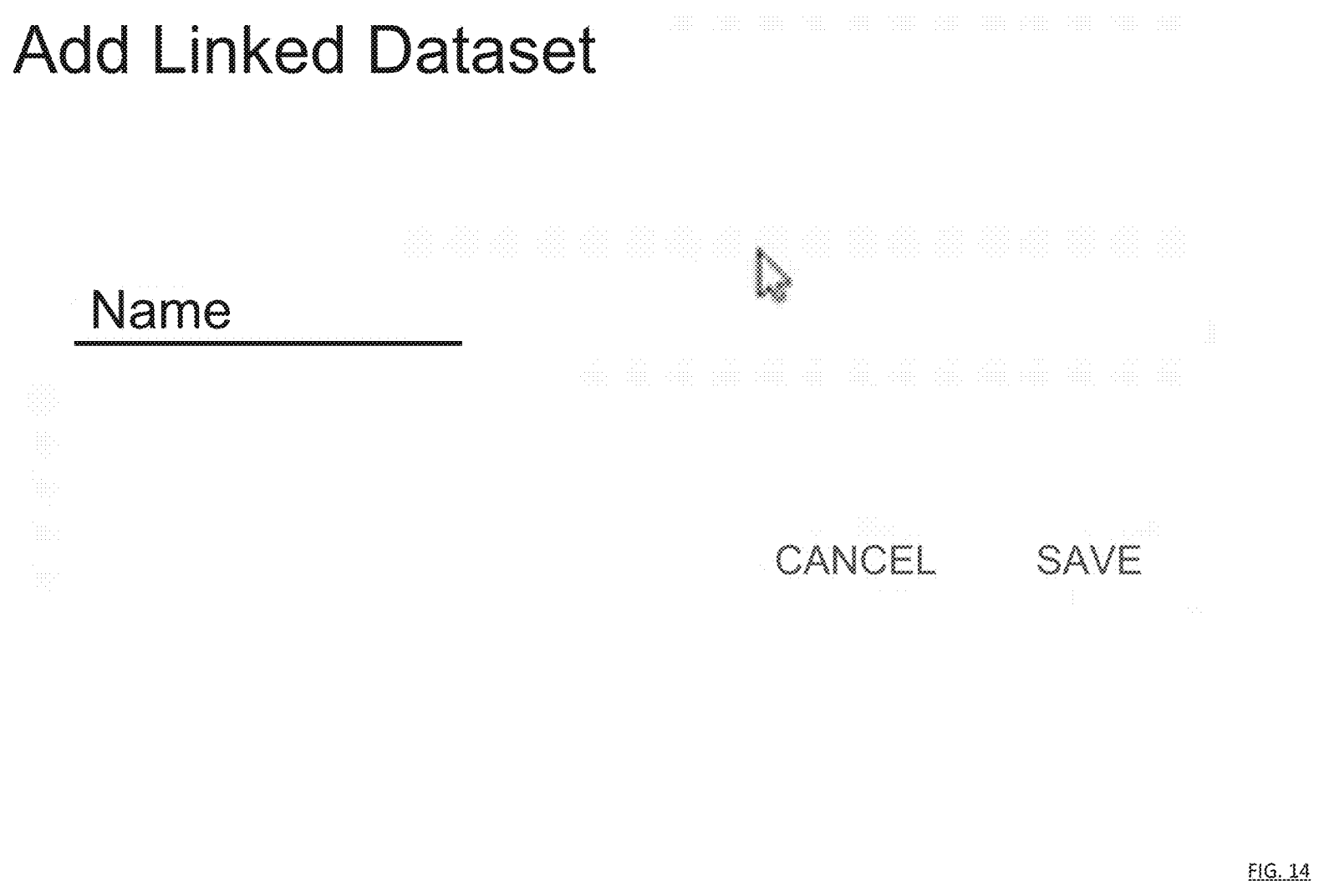

In a dashboard view of the CDM navigator as shown in FIG. 10, for example, users can see helpful information, such as requests created in the previous two weeks, the number of pending requests in different stages, and certain high level views of flagging of invalid codes. In order to establish linkage between the CDM and the OES a powerful, dynamic data engine can be used to process the information. FIGS. 11 through 15 illustrate examples of a "Configurations" section of the navigation software, in which various data analysis parameters can be configured and certain datasets can be linked for performing analysis functions of the transaction analysis system.

Figure 15:
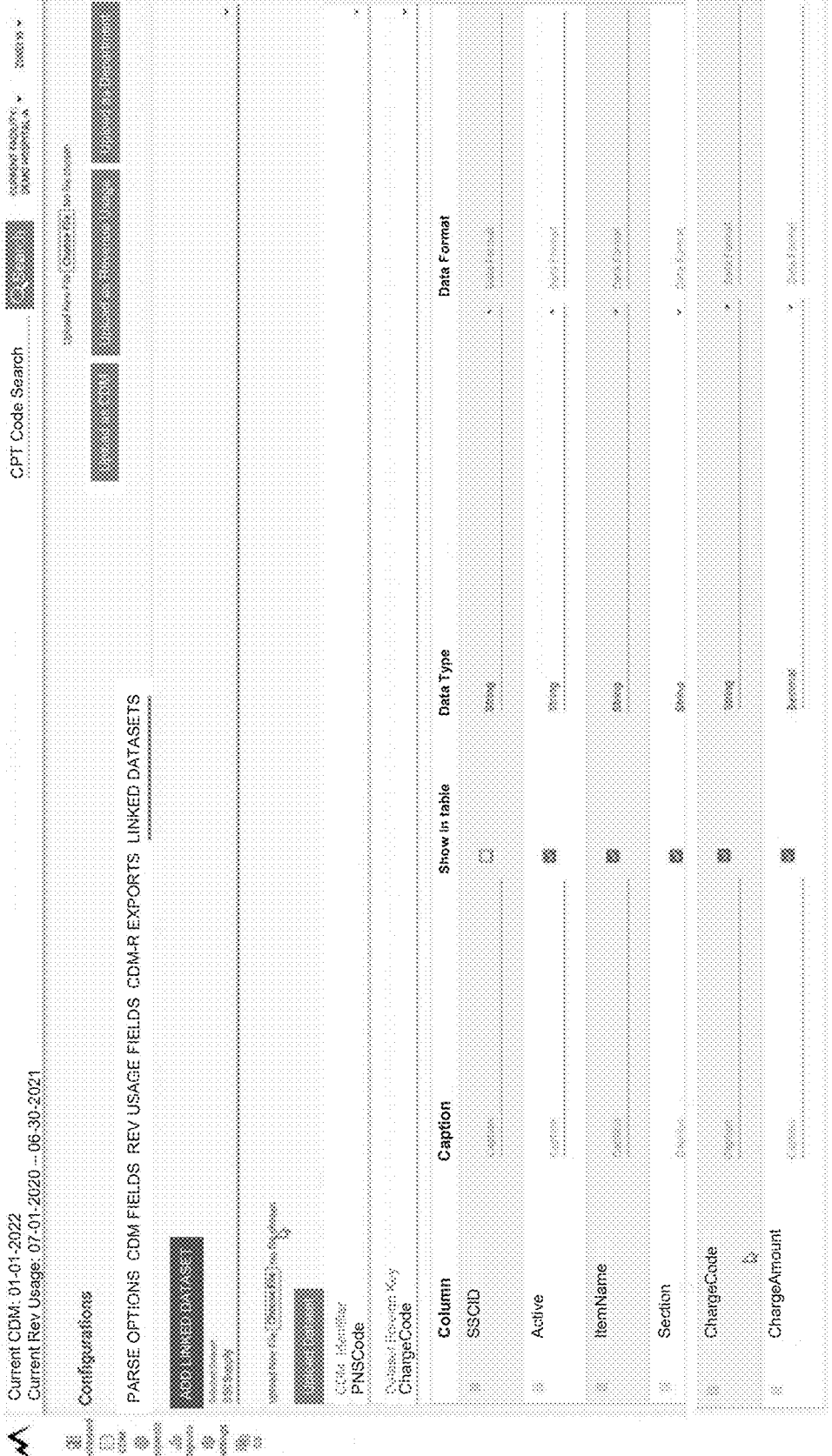
FIG. 15 is a screen display illustrating an example of an Order Entry Data Import user interface.

With reference to FIG. 15, accessing the CDM tab allows the user to find a file from the user's local directory, and then upload it as a CDM file. After the file has been uploaded, the system can automatically generate the various columns as configure with various parameters and can facilitate selection of a number of different flags. The PNSCode can be considered a CDM ID. It has a unique identifier in the chargemaster. The user can decide to display it in the CDM table, for example, or specify whether the field is modifiable. In other aspects, the status indicator indicates whether the charge code is active or inactive. Other fields help the user to understand whether it is a CPG code, for example, used for a procedure, billing purposes, or if it is a description that would be used to identify an inaccuracy of the service that has been described. After the CDM data has been loaded, a linked dataset screen facilitates upload of the order entry files, such as one called SSC Supply in the surgical care module, for example. After the file is uploaded, similar to how a CDM file is uploaded, the system can automatically generate column IDs as shown. The user can check boxes on the screen to let the system know which fields the user wants to include in the table for the user to see Some of the fields may be numeric that can be configured as decimals.

One of the key steps in the configuration for a linked dataset order entry system is to identify the linkage between a CDM file vs the order entry file. So, within every order entry file there can be a column that populates to see an ID. That column may have different names, such as charge code. In other systems, it may be called item ID, item number, or other names. The charge code can be used to link the item number back to the CDM. The file name for the CDM identifier may be called a PNSCode. With these two key data fields configured, the user can return to the CDM screen to perform the analysis, or the user can go to a "C3" view, where the system can display the information for a linked dataset. This includes all of the order entry system lines that are mapped to the CDM. So, in this C3 view the user can see the chargemaster information, the CDM identifier, the PNSCode, followed by status indicator, effective date, description, and so forth. This can provide linked data, such as revenue usage if it has been loaded. FIG. 15 illustrates a sample Order Entry Data Import user interface screen display.

The information can be filtered based on certain keywords. For example, one filter is any item that has screw in the description. The user can click on a desired item to look at the linkage information. In one example shown in FIGS. 16 through 19, the records linked to CDM ID (44100655) can be displayed. It can be seen that this screw is actually mapped to multiple implants within the order entry system. So, the screws are all configured with the same item name, but they have different sizes. This provides a helpful view to examine the linkage between the CDM and the multiple items that it could be linked to. It can be appreciated how this CDM navigator solution can provide a number of different reports to identify potential revenue linkage issues.

Figure 20:
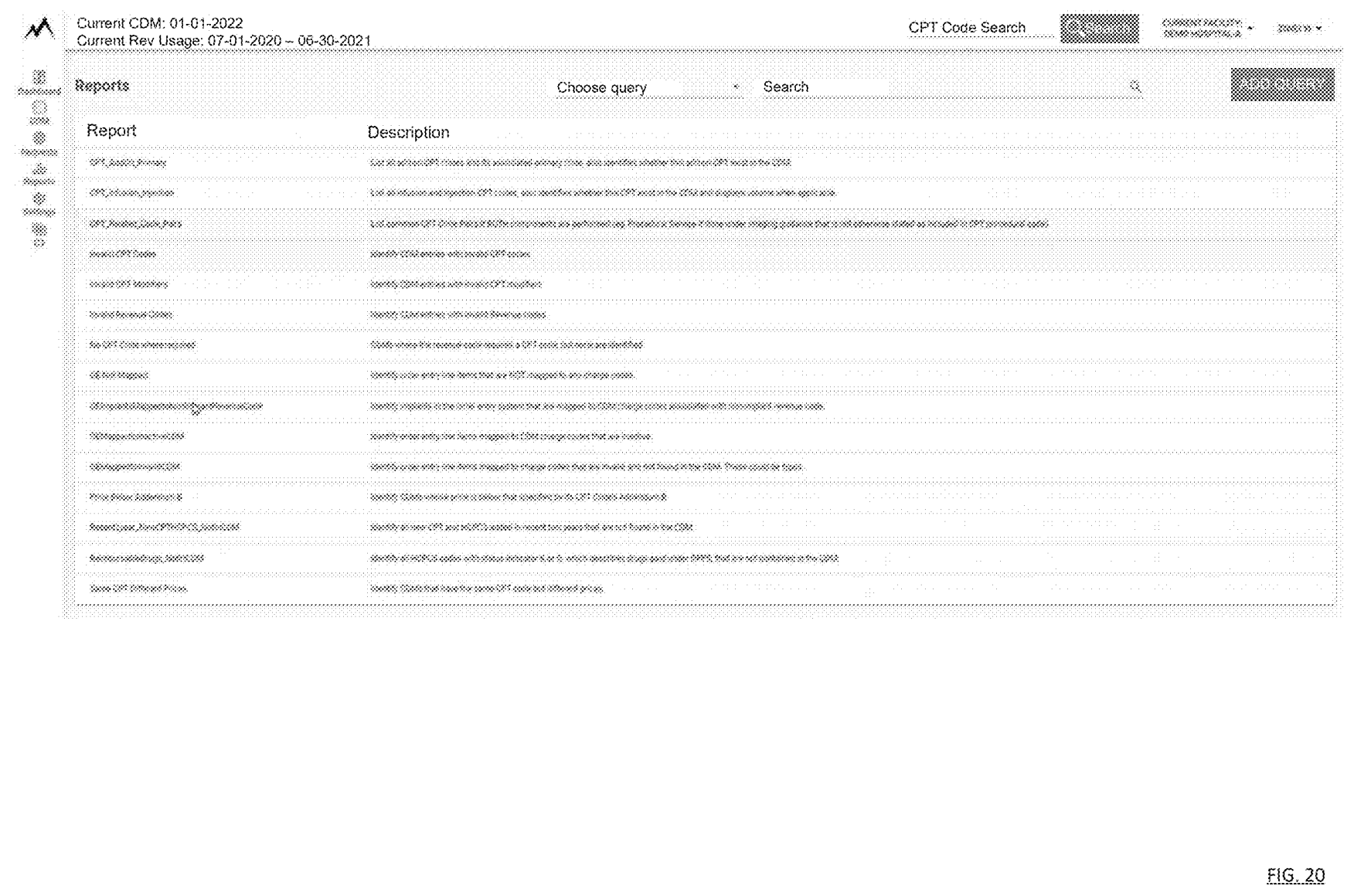

In the reporting section of the CDM navigator, as shown in the list displayed in FIG. 20, the user can see multiple reports loaded including order entry-related reports. Another example shown in FIG. 21 is an OE-not-mapped report which identifies the order entry line items that are not mapped to any charge code. The report can show each item with its own item number, item name described, and section which is describes what type of supply this is. In the charge code field, all of them are populated as null. So, there is no value attached to the order entry items. This means that, if the user orders any of these items, and if the user processes the item that has been utilized, then because it is not linked to any of the charge codes it will not generate a charge or revenue for the organization. The CDM navigator can be used to export the report and get a copy as an Excel file, and perform some additional analysis on it, or share it with another user.

In another example shown in FIG. 22, order entry line items that have been mapped to a CDM, but that still have problems, can be identified. In this case, the item is mapped to charge codes as shown, however, all of the charge codes are flagged as inactive. So, even though they were established with the CDM at one point, they have been deactivated for various different reasons. If the user tries to order the item and process it, there won't be any charges generated on the claim forms. Therefore, there will be missing revenue attached to these items. Once this report is generated, users can evaluate the item to determine if the organization is still using them, and if so, they can determine the replacement charge code existing in a chargemaster. If that can be identified, then these order entry items can be remapped to the new charge code. If the user cannot find a valid charge code in the CDM for the item, a brand new code can be built to avoid revenue loss. This report can be called an order-entry-map-to-inactive-CDM report.

Figure 23:
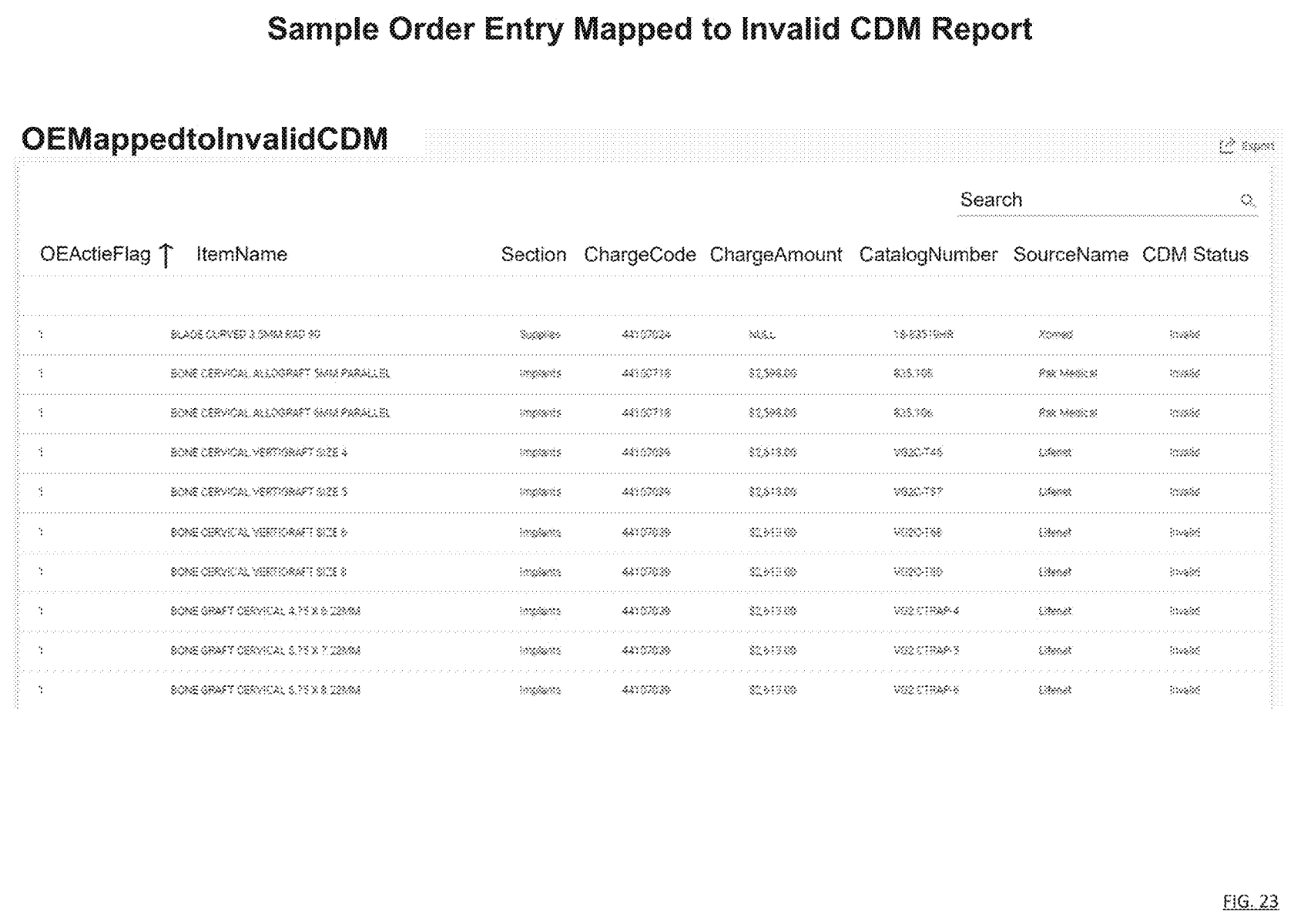

In another example shown in FIG. 23, a report can be generated to examine order entry items that appear to be mapped to a charge code, however, these charge codes are considered invalid. This means that the item was not found in the CDM at all. For example, the item may have an extra digit or other typographical error in its identifier, and this causes the linkage to become invalid. A user or the system can review these items to try to map them to an existing charge code, and/or to build a new charge code for them.

In another example, with reference to FIG. 24, a report called OE-implants-mapped-to-non-implements-revenue-codes can be generated in connection with an operating room (OR) supply module, for example. This report may include an item type which informs the user whether it is a catheter or an implant, or another type of supplies. For example, items flagged as implants can be reviewed to see if they are mapped to implant revenue codes (i.e., codes in the 275 to 278 range). As shown, in certain cases the report notes that certain items have been flagged as implants; however, they have been mapped with a regular routine supply revenue code, for example, or mapped to a pharmacy revenue code. Accordingly, these items may require additional review to correct either the supply assignment in the OR Supply module or their linkage to the CDM.

The examples presented herein can be intended to illustrate potential and specific implementations of the present invention. It can be appreciated that the examples can be intended primarily for purposes of illustration of the invention for those skilled in the art. No particular aspect or aspects of the examples can be necessarily intended to limit the scope of the present invention. For example, no particular aspect or aspects of the examples of system architectures, user interface layouts, algorithm use cases, or screen displays described herein are necessarily intended to limit the scope of the invention.

It is to be understood that the figures and descriptions of the present invention have been simplified to illustrate elements that can be relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore, the invention as may be defined by such means-plus-function claims, resides in the fact that the functionalities provided by the various recited means can be combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium. In certain embodiments, artificial intelligence techniques, machine learning algorithms, and/or rules-based algorithms may be employed as unconventional tools for performing the processes and executing the computer systems described herein.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual (e.g., cloud-based), permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth.

Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, processor, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to execution of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that can be located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, TypeScript, Ruby, PHP, and Perl. Various embodiments may be employed in a Lotus Notes environment, for example. Such software may be stored on any type of suitable computer-readable medium or media such as, for example, a magnetic or optical storage medium.

Thus, the execution and behavior of the embodiments can be described without specific reference to the actual software code. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, cellular network communication, power line communication, or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs) remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

As employed herein, an application server may be a server that hosts an API to expose business logic and business processes for use by other applications. Examples of application servers include J2EE or Java EE 5 (Oracle) application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java). Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture. Certain embodiments of the invention may employ web servers such as Apache web servers, for example.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Various embodiments may be described herein in the general context of computer executable instructions, such as software, program modules, and/or engines being executed by a computer. Generally, software, program modules, and/or engines include any software element arranged to perform particular executions or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where executions can be performed by one or more remote processing devices that can be linked through a communications network. In a distributed computing environment, software, program modules, and/or engines may be located in both local and remote computer storage media including memory storage devices.

Although some embodiments may be illustrated and described as comprising functional components, software, engines, and/or modules performing various executions, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various executions of one or more embodiments. In various embodiments, for example, the article of manufacture may comprise a magnetic disk, optical disk, flash memory or firmware containing computer program instructions suitable for execution by an application specific processor.

Additionally, it is to be appreciated that the embodiments described herein illustrate example implementations, and that the functional elements, logical blocks, modules, and circuits elements may be implemented in various other ways which can be consistent with the described embodiments. Furthermore, the executions performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Reference to "one embodiment" or "an embodiment" means that a particular feature, structure, or characteristic described in connection with the embodiment is comprised in at least one embodiment. The appearances of the phrase "in one embodiment" or "in one aspect" in the specification can be not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms can be not necessarily intended as synonyms for each other. For example, some embodiments may be described using the terms "com1ected" and/or "coupled" to indicate that two or more elements can be in direct physical or electrical contact with each other. The term "coupled," however, also may mean that two or more elements can be not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and can be comprised within the scope thereof. Furthermore, all examples and conditional language recited herein can be principally intended to aid the reader in understanding the principles described in the present disclosure and the concepts contributed to furthering the art, and can be to be construed as being without limitation to such specifically recited examples and conditions. Moreover, all statements herein reciting principles, aspects, and embodiments as well as specific examples thereof, can be intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by general purpose hardware as discussed above, as an alternative the same may also be embodied in dedicated hardware or a combination of software, hardware and/or dedicated hardware. If embodied in dedicated hardware, each can be implemented as a circuit or state machine that employs any one of or a combination of a number of technologies. These technologies may include, but can be not limited to, discrete logic circuits having logic gates for implementing various logic functions upon an application of one or more data signals, application specific integrated circuits having appropriate logic gates, or other components, etc. Such technologies can be generally well known by those of ordinary skill in the art and, consequently, can be not described in detail herein.

The flow charts and methods described herein show the functionality and execution of various implementations. If embodied in software, each block, step, or action may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s). Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be omitted or not performed. It is understood that all such variations can be within the scope of the present disclosure.

The terms "a" and "an" and "the" and similar referents used in the context of the present disclosure (especially in the context of the following claims) can be to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as though it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein can be not to be construed as limitations. Each group member may be referred to and claimed individually or in any combination with other members of the group or other elements found herein. It is anticipated that one or more members of a group may be comprised in, or deleted from, a group for reasons of convenience and/or patentability.

In various embodiments of the present invention, different types of artificial intelligence tools and techniques can be incorporated and implemented. Search and optimization tools including search algorithms, mathematical optimization, and evolutionary computation methods can be used for intelligently searching through many possible solutions. For example, logical operations can involve searching for a path that leads from premises to conclusions, where each step is the application of an inference rule. Planning algorithms can search through trees of goals and subgoals, attempting to find a path to a target goal, in a process called means-ends analysis.

Heuristics can be used that prioritize choices in favor of those more likely to reach a goal and to do so in a shorter number of steps. In some search methodologies heuristics can also serve to eliminate some choices unlikely to lead to a goal. Heuristics can supply a computer system with a best estimate for the path on which the solution lies. Heuristics can limit the search for solutions into a smaller sample size, thereby increasing overall computer system processing efficiency.

Propositional logic can be used which involves truth functions such as "or" and "not" search terms, and first-order logic can add quantifiers and predicates, and can express facts about objects, their properties, and their relationships with each other. Fuzzy logic assigns a degree of truth (e.g., between 0 and 1) to vague statements which may be too linguistically imprecise to be completely true or false. Default logics, non-monotonic logics and circumscription are forms of logic designed to help with default reasoning and the qualification problem. Several extensions of logic can be used to address specific domains of knowledge, such as description logics, situation calculus, event calculus and fluent calculus (for representing events and time), causal calculus, belief calculus (belief revision); and modal logics. Logic for modeling contradictory or inconsistent statements arising in multi-agent systems can also be used, such as paraconsistent logics.

Probabilistic methods can be applied for uncertain reasoning, such as Bayesian networks, hidden Markov models, Kalman filters, particle filters, decision theory, and utility theory. These tools and techniques help the system execute algorithms with incomplete or uncertain information. Bayesian networks are tools that can be used for various problems: reasoning (using the Bayesian inference algorithm), learning (using the expectation-maximization algorithm), planning (using decision networks), and perception (using dynamic Bayesian networks). Probabilistic algorithms can be used for filtering, prediction, smoothing and finding explanations for streams of data, helping perception systems to analyze processes that occur over time (e.g., hidden Markov models or Kalman filters). Artificial intelligence can use the concept of utility as a measure of how valuable something is to an intelligent agent. Mathematical tools can analyze how an agent can make choices and plan, using decision theory, decision analysis, and information value theory. These tools include models such as Markov decision processes, dynamic decision networks, game theory and mechanism design.

The artificial intelligence techniques applied to embodiments of the invention may leverage classifiers and controllers. Classifiers are functions that use pattern matching to determine a closest match. They can be tuned according to examples known as observations or patterns. In supervised learning, each pattern belongs to a certain predefined class which represents a decision to be made. All of the observations combined with their class labels are known as a data set. When a new observation is received, that observation is classified based on previous experience. A classifier can be trained in various ways; there are many statistical and machine learning approaches. The decision tree is one kind of symbolic machine learning algorithm. The naive Bayes classifier is one kind of classifier useful for its scalability, in particular. Neural networks can also be used for classification. Classifier performance depends in part on the characteristics of the data to be classified, such as the data set size, distribution of samples across classes, dimensionality, and the level of noise. Model-based classifiers perform optimally when the assumed model is an optimized fit for the actual data. Otherwise, if no matching model is available, and if accuracy (rather than speed or scalability) is a primary concern, then discriminative classifiers (e.g., SVM) can be used to enhance accuracy.

A neural network is an interconnected group of nodes which can be used in connection with various embodiments of the invention, such as execution of various methods, processes, or algorithms disclosed herein. Each neuron of the neural network can accept inputs from other neurons, each of which when activated casts a weighted vote for or against whether the first neuron should activate. Learning achieved by the network involves using an algorithm to adjust these weights based on the training data. For example, one algorithm increases the weight between two connected neurons when the activation of one triggers the successful activation of another. Neurons have a continuous spectrum of activation, and neurons can process inputs in a non-linear way rather than weighing straightforward votes. Neural networks can model complex relationships between inputs and outputs or find patterns in data. They can learn continuous functions and even digital logical operations. Neural networks can be viewed as a type of mathematical optimization which performs a gradient descent on a multi-dimensional topology that was created by training the network. Another type of algorithm is a backpropagation algorithm. Other examples of learning techniques for neural networks include Hebbian learning, group method of data handling (GMDH), or competitive learning. The main categories of networks are acyclic or feedforward neural networks (where the signal passes in only one direction), and recurrent neural networks (which allow feedback and short-term memories of previous input events). Examples of feedforward networks include perceptrons, multi-layer perceptrons, and radial basis networks.

Deep learning techniques applied to various embodiments of the invention can use several layers of neurons between the network's inputs and outputs. The multiple layers can progressively extract higher-level features from the raw input. For example, in image processing, lower layers may identify edges, while higher layers may identify the concepts relevant to a human such as digits or letters or faces. Deep learning may involve convolutional neural networks for many or all of its layers. In a convolutional layer, each neuron receives input from only a restricted area of the previous layer called the neuron's receptive field. This can substantially reduce the number of weighted connections between neurons. In a recurrent neural network, the signal will propagate through a layer more than once. A recurrent neural network (RNN) is another example of a deep learning technique which can be trained by gradient descent, for example.

While various embodiments of the invention have been described herein, it should be apparent, however, that various modifications, alterations, and adaptations to those embodiments may occur to persons skilled in the art with the attainment of some or all of the advantages of the present invention. The disclosed embodiments can be therefore intended to include all such modifications, alterations, and adaptations without departing from the scope and spirit of the present invention as described and claimed herein.

What is claimed is:

1. A computer-implemented method for analyzing health care procedure related transactions of a health care entity, the method comprising:

importing, by a transaction analysis computer system including at least one electronic computer processor and at least one computer-readable medium, at least the following information:

at least a portion of a charge description master (CDM) file containing multiple CDM healthcare data items, at least a portion of an order entry system (OES) file containing multiple OES healthcare data items, and at least a portion of a CDM-to-OES cross-reference data file;

the transaction computer system programmed with at least one dynamic data engine configured for processing multiple data models adaptable to changes in data structures associated with the imported information;

creating, by the transaction analysis system applying the CDM-to-OES cross-reference data file to the CDM data items file and the OES data items file, a linked data items file;

analyzing, by the transaction analysis system, the linked data items file, wherein the analyzing comprises:

reading at least one linked line item of the linked data items file, analyzing a CDM data portion of the linked line item, analyzing an OES data portion of the linked line item, and comparing the linked CDM data portion to the linked OES data portion of the linked line item for determining at least one similarity or difference between the CDM data portion and the OES data portion, wherein the comparing further comprises:

analyzing the CDM data portion of the linked line item for determining an active or inactive status of a CDM data item, analyzing the CDM data portion of the linked line item for determining a chargeability status of a CDM data item, and generating a report in response to determining at least one similarity or difference between the OES data portion and the CDM data portion, the report including at least one indication of a discrepancy which needs to be corrected; and executing, by the transaction analysis system, at least one or more of:

changing at least a portion of the OES data portion and/or at least a portion of the CDM data portion in response to determining at least one similarity or difference between the linked OES data portion and the linked CDM data portion; and/or mapping at least one CDM data item to at least one OES data item in response to identifying the CDM data item as unmapped to any OES data item.

2. The method of claim 1, further comprising analyzing the OES data portion of the linked line item for determining an active or inactive status of an OES data item.

3. The method of claim 1, further comprising analyzing the OES data portion of the linked line item for determining a chargeability status of an OES data item.

4. The method of claim 1, further comprising comparing the OES data portion to the CDM data portion of the linked line item for determining at least one similarity or difference between the linked OES data portion and the linked CDM data portion.

5. The method of claim 1, further comprising determining at least one similarity or difference between the linked CDM data portion and the linked OES data portion by comparing at least a portion of a description associated with the linked CDM data portion to at least a portion of a description associated with the linked OES data portion.

6. The method of claim 1, further comprising determining at least one similarity or difference between the linked CDM data portion and the linked OES data portion by comparing at least a portion of a unit of measure associated with the linked CDM data portion to at least a portion of a unit of measure associated with the linked OES data portion.

7. The method of claim 1, further comprising identifying at least one OES data item unmapped to any CDM data item.

8. The method of claim 7, further comprising determining an active or inactive status of the unmapped OES data item.

9. The method of claim 7, further comprising determining a chargeability status of the unmapped OES data item.

10. The method of claim 1, further comprising identifying at least one CDM data item unmapped to any OES data item.

11. The method of claim 10, further comprising determining an active or inactive status of the unmapped CDM data item.

12. The method of claim 10, further comprising determining a chargeability status of the unmapped CDM data item.

13. The method of claim 1, further comprising using an artificial intelligence module for analyzing the CDM data portion of the linked line item.

14. The method of claim 1, further comprising using an artificial intelligence module for analyzing the OES data portion of the linked line item.

15. The method of claim 1, further comprising using an artificial intelligence module for comparing the CDM data portion to the OES data portion of the linked line item for determining at least one similarity or difference between the linked CDM data portion and the linked OES data portion.

16. The method of claim 15, further comprising using an artificial intelligence module for comparing the OES data portion to the CDM data portion of the linked line item for determining at least one similarity or difference between the linked OES data portion and the linked CDM data portion.

17. The method of claim 1, further comprising communicating at least one electronic mail notification in response to generating the report, the notification including the at least one indication of a discrepancy which needs to be corrected.

* * * * *